US010960068B2

(12) United States Patent
Hargis et al.

(10) Patent No.: US 10,960,068 B2
(45) Date of Patent: *Mar. 30, 2021

(54) VACCINE AND METHODS TO REDUCE CAMPYLOBACTER INFECTION

(71) Applicant: THE BOARD OF TRUSTEES OF THE UNIVERSITY OF ARKANSAS, Little Rock, AR (US)

(72) Inventors: Billy Hargis, Fayetteville, AR (US); Neil R. Pumford, Bentonville, AR (US); Young Min Kwon, West Fork, AR (US); Sherryll Layton, Rogers, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/623,196

(22) Filed: Feb. 16, 2015

(65) Prior Publication Data
US 2015/0190496 A1    Jul. 9, 2015

Related U.S. Application Data

(63) Continuation of application No. 13/702,827, filed as application No. PCT/US2011/039832 on Jun. 9, 2011, now Pat. No. 8,961,990.

(60) Provisional application No. 61/353,039, filed on Jun. 9, 2010.

(51) Int. Cl.
*A61K 39/12* (2006.01)
*A61K 39/02* (2006.01)
*C07K 14/205* (2006.01)
*A61K 39/00* (2006.01)

(52) U.S. Cl.
CPC ............ *A61K 39/12* (2013.01); *A61K 39/105* (2013.01); *C07K 14/205* (2013.01); *A61K 2039/523* (2013.01); *A61K 2039/53* (2013.01); *A61K 2039/55516* (2013.01)

(58) Field of Classification Search
None
See application file for complete search history.

(56) References Cited

U.S. PATENT DOCUMENTS

| | | | |
|---|---|---|---|
| 5,683,700 A | 11/1997 | Charles et al. | |
| 5,747,309 A | 5/1998 | Allan et al. | |
| 5,962,406 A | 10/1999 | Armitage et al. | |
| 5,981,724 A | 11/1999 | Armitage et al. | |
| 6,087,329 A | 7/2000 | Armitage et al. | |
| 6,190,669 B1 | 2/2001 | Noriega et al. | |
| 6,264,951 B1 | 7/2001 | Armitage et al. | |
| 6,306,387 B1 | 10/2001 | Galan | |
| 6,410,711 B1 | 6/2002 | Armitage et al. | |
| 6,479,258 B1 | 11/2002 | Short | |
| 6,713,279 B1 | 3/2004 | Short | |
| 6,902,906 B1 | 6/2005 | Chatfield | |
| 6,923,957 B2 | 8/2005 | Lowery et al. | |
| 6,923,958 B2 | 8/2005 | Xiang et al. | |
| 6,936,425 B1 | 8/2005 | Hensel et al. | |
| 6,969,609 B1 | 11/2005 | Schlom et al. | |
| 7,087,573 B1 | 8/2006 | Lazarus et al. | |
| 7,332,298 B2 | 2/2008 | Kornbluth | |
| 7,371,392 B2 | 5/2008 | Tripp et al. | |
| 7,405,270 B2 | 7/2008 | Armitage et al. | |
| 7,495,090 B2 | 2/2009 | Prussak et al. | |
| 7,842,501 B2 | 11/2010 | Cai et al. | |
| 7,928,213 B2 | 4/2011 | Prussak et al. | |
| 8,604,178 B2 | 12/2013 | Bottje et al. | |
| 8,956,618 B2 | 2/2015 | Berghman et al. | |
| 8,956,849 B2 | 2/2015 | Bottje et al. | |
| 2001/0021386 A1 | 9/2001 | Nuijten et al. | |
| 2003/0165538 A1 | 9/2003 | Goldman et al. | |
| 2004/0006006 A9 | 1/2004 | Armitage et al. | |
| 2004/0047873 A1 | 3/2004 | Al-Shamkhani et al. | |
| 2004/0053841 A1 | 3/2004 | Tracey et al. | |
| 2004/0141948 A1 | 7/2004 | O'Keefe | |
| 2004/0156851 A1 | 8/2004 | Newman | |
| 2004/0203039 A1 | 10/2004 | Hensel et al. | |
| 2005/0181994 A1 | 8/2005 | Chamberlain et al. | |
| 2005/0226888 A1 | 10/2005 | Deisseroth et al. | |
| 2006/0014248 A1 | 1/2006 | Marshall et al. | |
| 2006/0078994 A1 | 4/2006 | Healey et al. | |
| 2006/0121047 A1 | 6/2006 | Tracey | |

(Continued)

FOREIGN PATENT DOCUMENTS

| | | |
|---|---|---|
| WO | WO 1993/008207 | 4/1993 |
| WO | WO 1995/014487 | 6/1995 |

(Continued)

OTHER PUBLICATIONS

Kimura et al. (Journal of Immunological Methods, vol. 361, pp. 21-30).*
Greenspan et al. (Nature Biotechnology 7: 936-937, 1999).*
Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Mauriello, E.M.F. et al., "Display of heterologous antigens on the Bacillus subtilis Spore coat using CotC as a fusion partner," (2004) Vaccine 22(9-10):1177-1187.

(Continued)

Primary Examiner — Robert A Zeman
(74) Attorney, Agent, or Firm — Quarles & Brady LLP

(57) ABSTRACT

Vaccine vectors and methods for enhancing resistance to *Campylobacter* infection or for enhancing the immune response to *Campylobacter* are provided herein. The vaccine vectors include a first polynucleotide which encodes an antigenic polypeptide selected from SEQ ID NO: 7-9 or a fragment thereof. The vector may also include an immunostimulatory polypeptide. The methods include administering the vaccine vectors to a subject.

14 Claims, 10 Drawing Sheets
Specification includes a Sequence Listing.

(56) References Cited

U.S. PATENT DOCUMENTS

| | | | |
|---|---|---|---|
| 2006/0233829 | A1 | 10/2006 | Curtiss |
| 2006/0286074 | A1 | 12/2006 | Tang et al. |
| 2007/0025982 | A1 | 2/2007 | Ledbetter et al. |
| 2007/0082400 | A1 | 4/2007 | Healey et al. |
| 2007/0128183 | A1* | 6/2007 | Meinke et al. ............ 424/130.1 |
| 2007/0128223 | A1 | 6/2007 | Tang et al. |
| 2007/0237779 | A1 | 10/2007 | Ledbetter et al. |
| 2007/0249553 | A1 | 10/2007 | Newell et al. |
| 2008/0004207 | A1 | 1/2008 | Tsung et al. |
| 2008/0075728 | A1 | 3/2008 | Newman |
| 2008/0124320 | A1 | 5/2008 | O'Keefe |
| 2008/0305120 | A1 | 12/2008 | Messmer et al. |
| 2009/0004194 | A1 | 1/2009 | Kedl |
| 2010/0040608 | A1 | 2/2010 | Wahren-Herlenius et al. |
| 2010/0047231 | A1 | 2/2010 | Zabaleta Azpiroz et al. |
| 2010/0112002 | A1 | 5/2010 | Lien et al. |
| 2010/0233152 | A1 | 9/2010 | Bullerdiek |
| 2010/0291109 | A1 | 11/2010 | Kedl |
| 2010/0292309 | A1 | 11/2010 | Vile et al. |
| 2011/0020318 | A1 | 1/2011 | Tracey et al. |
| 2011/0159026 | A1 | 6/2011 | Bottje et al. |
| 2012/0282291 | A1* | 11/2012 | Berghman et al. ........ 424/192.1 |

FOREIGN PATENT DOCUMENTS

| | | |
|---|---|---|
| WO | WO 1996/026735 | 9/1996 |
| WO | WO 1996/040918 | 12/1996 |
| WO | WO 1999/027948 | 6/1999 |
| WO | WO 1999/032138 | 7/1999 |
| WO | WO 1999/059609 | 11/1999 |
| WO | WO 2000/063395 | 10/2000 |
| WO | WO 2000/063405 | 10/2000 |
| WO | WO 2001/042298 | 6/2001 |
| WO | WO 2001/056602 | 8/2001 |
| WO | WO 2002/036769 | 5/2002 |
| WO | WO 2002/092773 | 11/2002 |
| WO | WO 03026691 A2 * | 4/2003 |
| WO | WO 2003/099340 | 12/2003 |
| WO | WP 2004/009615 | 1/2004 |
| WO | WO 2004/046338 | 6/2004 |
| WO | WO 2004/046345 | 6/2004 |
| WO | WO 2005/025604 | 3/2005 |
| WO | WO 2005/035570 | 4/2005 |
| WO | WO 2005/049641 | 6/2005 |
| WO | WO 2005/058950 | 6/2005 |
| WO | WO 2005/113598 | 12/2005 |
| WO | WO 2006/012373 | 2/2006 |
| WO | WO 2006/042177 | 4/2006 |
| WO | WO 2006/046017 | 5/2006 |
| WO | WO 2006/105972 | 10/2006 |
| WO | WO 2007/011606 | 1/2007 |
| WO | WO 2007/042583 | 4/2007 |
| WO | WO 2007/054658 | 5/2007 |
| WO | WO 2007/056266 | 5/2007 |
| WO | WO 2007/103048 | 9/2007 |
| WO | WO 2007/117682 | 10/2007 |
| WO | WO 2008/036675 | 3/2008 |
| WO | WO 2008/109825 | 9/2008 |
| WO | WO 2009/059018 | 5/2009 |
| WO | WO 2009/059298 | 5/2009 |
| WO | WO 2011/091255 | 7/2011 |

OTHER PUBLICATIONS

Mendoza, R.B. et al., "Cutting edge: Immunostimulatory effects of a plasmid expressing CD40 ligand (CD154) on gene immunization," Journal of Immunology (1997) 159(12):5777-5781.

Miga, A. et al., "The role of CD40-CD154 interactions in the regulation of cell mediated immunity," Immunol. Invest. (2000) 29:111-114.

Mogensen, T.H., "Pathogen recognition and inflammatory signaling in innate immune defenses," Clin. Microbiol. Rev. (2009) 22(2):240-273.

Mohamadzadeh, M. et al., "Targeting mucosal dendritic cells with microbial antigens from probiotic lactic acid bacteria," Expert Rev. Vaccines (2008) 7(2)163-174.

Moyle, P.M. et al., "Mucosal immunisation: adjuvants and delivery systems." Curr. Drug Deliv. (2004) 1(4):385-396.

Nakajima, A. et al., "Antitumor effect of CD40 ligand: Elicitation of local and systemic antitumor responses by IL-12 and B7," (1998) Journal of Immunology 161:1901-1907.

O'Callaghan, D. et al., "Immunogenicity of foreign peptide epitopes expressed in bacterial envelope proteins," Research in Microbiology (1990) 141:963-969.

Ochoa-Reparaz, J. et al., "Humoral immune reponse in hens naturally infected with *Salmonella enteritidis* against outer membrane proteins and other surface structural antigens," (2004) Vet. Res. 35:291-298.

Pasetti, M. et al., "Animal models paving the way for clinical trials of attenuated *Salmonella enterica* servoar Typhi live oral vaccines and live vectors," Vaccine (2003) 21:401-418.

Pawelec, D. et al., "Cloning and characterization of a Campylobacter jejuni 72Dz/92 gene encoding a 30 kDa immunopositive protein, component of the ABC transport system; expression of the gene in avirulent *Salmonella typhimurium*," FEMS Immuno. Med. Microbiol. (1997) 19(2):137-50.

Pawelec, D. et al., "Genetic diversity of the Campylobacter genes coding immunodominant proteins," FEMS Microbiol. Lett. (2000) 185(1):43-49.

Pisetsky, D.S. et al., "High-mobility group box protein 1 (HMGB1): an alarmin mediating the pathogenesis of rheumatic disease," Arthritis Res. Ther. (2008) 10(3):209.

Prokhorova, T.A. et al., "Novel surface polypeptides of Campylobacter jejuni as traveller's diarrhoea vaccine candidates discovered by proteomics," Vaccine (2006) 24(40-41):6446-6455.

Rabsch, W. et al., "Competitive exclusion of *Salmonella enteritidis* by *Salmonella gallinarum* in poultry," Emerging Inf. Diseases (2000) 6(5):443-448.

Rovere-Querini, P. et al., "HMGB1 is an endogenous immune adjuvant released by necrotic cells," EMBO Rep. (2004) 5(8):825-830.

Russmann, H. et al., "Delivery of epitopes by the *Salmonella* type III secretion system for vaccine development," Science (1998) 281 (5376):565-568.

Saenz, R. et al., "HMGB1-derived peptide acts as adjuvant inducing immune responses to peptide protein antigen," (2010) Vaccine 28(47):7556-7562.

Schrotz-King, P. et al., "Campylobacter jejuni proteomics for new travellers' diarrhoea vaccines," Travel Med. Infect. Dis. (2007) 5(2):106-109.

Sizemore, D.R. et al., "Live, attenuated *Salmonella typhimurium* vectoring: Campylobacter antigens," Vaccine (2006) 24(18):3793-3803.

Su, G.F. et al., "Construction of stable LamB-Shiga toxin B subunit hybrids: analysis of expression in *Salmonella typhimurium* aroA strains and stimulation of B subunit-specific mucosal and serum antibody responses," Infect Immun (1992) 60(8):3345-3359.

Swayne, D.E., "Vaccines for List A poultry diseases: emphasis on avian influenza," Dev. Biol. (2003) 114:201-212.

Tregaskes, C.A. et al., "Conservation of biological properties of the CD40 ligand, CD154 in a non-mammalian vertebrate," Dev. Comp. Immunol. (2005) 29:361-374.

Ulloa, L. et al., "High-mobility group box 1 (HMGB1) protein: friend and foe." Cytokine Growth Factor Rev. (2006) 17(3):189-201.

UniProt_A3Z125, CjaA protein, last modified Apr. 3, 2007 [online]. Retrieved on Nov. 1, 2011 from the Internet: <URL: http://www.uniprot.org/uniprot/A3Z125>.

Vega, M.L. et al., "A *Salmonella typhi* OmpC fusion protein expressing the CD154 Trp140-Ser149 amino acid strand binds CD40 and activates a lymphoma B-cell line," Immunol. (2003) 110:206-216.

Verjans, G.M. et al., "Intracellular processing and presentation of T cell epitopes, expressed by recombinant *Echerichia coli* and *Salmonella typhimurium*, to human T cells," Eur J Immunol (1995) 25(2):405-410.

(56) References Cited

OTHER PUBLICATIONS

Vierira-Pinto, M. et al.., "Occurrence of *Salmonella* in the ileum, ileocolic lymph nodes, tonsils, mandibular lymph nodes and carcasses of pigs slaughtered for consumption," J Vet Med B Infection Dis Vet Public Health (2005) 52(10)476-81.
Wang, J. et al., "Immunogenicity of viral B-cell epitopes inserted into two surface loops of the *Escherichia coli* K12 LamB protein and expressed in an attenuated aroA strain of *Salmonella typhimurium*," Vaccine (1999) 17(1)1.12.
Wyszynska, A. et al., "Oral immunization of chickens with avirulent *Salmonella* vaccine streain earring C. Jejuni 72Dz/92 cjaA gene elicits specific humoral immune response associated with protection against challenge with wild-type Campylobacter," Vaccine (2004) 22(11-12):1379-1389.
Xu, Y. et al., "The role of CD40-CD154 interaction in cell immunoregulation," J. Biomed. Sci. (2004) 11:426-438.
International Search Report and Written Opinion for international Patent Application No. PCT/US2011/022062 dated Mar. 29, 2011 (16 pages).
International Search Report and Written Opinion for International Patent Application No. PCT/US2011/039832 dated Nov. 23, 2011 (23 pages).
Extended European Search Report for European Patent Application No. 11793174.1 dated Oct. 9, 2013 (12 pages).
Office Action for U.S. Appl. No. 13/702,827 dated Oct. 30, 2013 (15 pages).
Office Action for U.S. Appl. No. 13/702,827 dated Jun. 26, 2014 (28 page).
Duc, L.H. et al., "Bacterial Spores as Vaccine Vehicles," Infection and Immunity (2003) 71(5): 2810-2818.
Hoang, T.H. et al., "Recombinant Bacillus subtilis Expressing the Clostridium perfringens Alpha Toxoid is a Candidate Orally Delivered Vaccine against Necrotic Enteritis," Infection and immunity (2008) 76(11): 5257-5265.
Muthumani, G. et al., "Co-immunization with an optimized plasmid-encoded immune stimulatory interleukin, high-mobility group box 1 protein, results in enhanced interferon-y secreation by antigen-specific CD8 T cells," Immunology (2009) 128: e612-e620.
Uyen, N.Q. et al., "Enhanced immunisation and expression strategies using bacterial spores as heat-stable vaccine delivery vehicles," Vaccine (2007) 25 356-365.
Agterberg, M. et al., "Outer membrane protein PhoE as a carrier the exposure of foreign antigenic determinants at the bacterial cell surface," Antonio Van Leeuwenhoek (1991) 59(4):249-262.
al-Ramadi, B. K. et al., "Induction of innate immunity IL-2 expressing *Salmonella* confers protection against lethal challenge," Mol. Immunol. (2003) 39:763-770.
al-Ramadi, B. K, et al., "Influence of vector-encoded cytokines on anti-*Salmonella* immunity: divergent effects of interleukin-2 and tumor necrosis factor alpha," Infect. Immun. (2001) 69:3960-3988.
Andersson, U. et al., "HMGB1 is a therapeutic target for sterile inflammation and infection," Annu. Rev. Immunol. (2011) 29:139-162.
Babu, U., el al., "*Salmonella enteritidis* clearance and immune responses in chickens following *Salmonella* vaccination and challenge," Vet. Immunol. Immunopathol. (2004)101:251-257.
Barr, T.A. et al., "A potent adjuvant effect of CD40 antibody attached to antigen," Immunology (2003) 109:87-92.
Barrow, P. A., et al., "Reduction in faecal excretion of *Salmonella typhimurium* strain F98 in chickens vaccinated with live and killed S. typhimurium organisms," Epidemiol. Infect. (1990) 104:413-426.
Blomfield, I.C. et al., "Allelic exchange in *Escherichia coli* using the Bacillus subtilis sacB gene and a temperature-sensitive pSC101 replicon," Mol Microbiol (1991) 5(6):1447-1457.
Buckley, A.M. et al., "Evaluation of live-attenuated *Salmonella* vaccines expressing Campylobacter antigens for control of C. jejuni in poultry," (2010) Vaccine 28(4):1094-1105.
Burnens, A. et al., "Identification and characterization or an immunogenic outer membrane protein of Campylobacter jejuni," J. Clin. Microbial. (1995) 33(11):2826-2832.

Charbit, A. et al., "Probing the topology of a bacterial membrane protein by genetic insertion of a foreign epitope; expression at the cell surface," EMBO J (1986) 5(11):3029-3037.
Charbit, A. et al., "Versatility of a vector for expressing foreign polypeptides at the surface of gram-negative bacteria," Gene (1988) 70(1):181-189.
Chatfield et al., "The development of oral vaccines based on live attenuated *Salmonella* strains." FEMS Immunol. Med. Microbiol. (1993) 7:1-7.
Cole, K. et al., "Evaluation of a novel recombinant *Salmonella* vaccine vector for avian influenza," Poultry Science (2007) 86(Supp. 1):585-586.
Cox, M.M. et al., "Scarless and site-directed mutagenesis in *Salmonella enteritidis* chromosome," BMC Biotech. (2007) 7(59):10 pages.
De Zoete, M.R. et al., "Vaccination of chickens against Campylobacter," Vaccine (2007).
Dumitriu, I.E. et al., "HMGB1; guiding immunity from within," Trends Immunol, (2005) 26(7):381-387.
Ellis, R.W., "New technologies for making vaccines," (1988) Vaccines, Chapter 29:568-574.
Faham, A. et al., "Liposomal Ag engrafted with peptides of sequence derived from HMGB1 induce potent Ag-specific and anti-tumour immunity," (2009) 27(42):5846-5854.
Farnell, M.D. et al., "Upregulation of oxidative burst and degranulation in chicken heterophils stimulated with probiotic bacteria," Poult. Sci. (2006) 85:1900-1906.
Fecteau, J.F. et al., "CD40 Stimulation of Human Peripheral B Lymphocytes: Distinct Response from Naïve and Memory Cells," J Immunol (2003) 171:4621-4629.
Fernandez-Cabezudo et al., "Evidence for the requirement for CD40-CD154 interactions in resistance to infections with attenuated *Salmonella*," J. Endotoxin Res. (2005) 11:395-399.
Gares, S.L. et al., "Immunotargeting with CD154 (CD40 ligand) enhances DNA vaccine reponses in ducks," Clin. Vaccine Immun. (2006) 13:958-965.
Gast, R.K. et al., "The relationship between the magnitude of the specific antibody response to experimental *Salmonella enteritidis* infection in laying hens and their production of contaminated eggs." Avian Diseases (2001) 45:425-431.
GenBank AF178849, "High mobility group protein HMG1 [Gallus gallas]," Sep. 27, 2000.
Grangette, C. et al., Protection against tetanus toxin after intragastric adminstration of two recombinant lactic acid bacteria: Impact and strain viability and in vivo persistence, Vaccine (2002) 20:3304-3309.
Greenspan, N.S. et al., "Defining epitopes: It's not as easy as it seems," Nature Biotechnol. (1999) 17:936-937.
Grewal, I.S. et al., "CD40 and CD154 in cell-mediated immunity," Annu. Rev. Immunology. (1998) 16:111-35.
Harcourt, J.L. et al., "CD40 ligand (CD154) improves the durability of respiratory syncytial virus DNA vaccination in BALB/c mice," Vaccine (2003) 21(21-22):2964-2979.
Hargis, B, "Live Recombinant *Salmonella* Vaccination with Novel Universal Antigen Presentation and Immune Protection," USDA Grant Project Status, Jan. 14, 2012.
Harris, H.E., et al., "Mini-review: The nuclear protin HMGB1 as a proinflammatory mediator," (2004) European J. of Immunology 34:1503-1512.
Hayes, L.J. et al., "Chlamydia trachomatis major outer membrane protein epitopes expressed as fusions with LamB in an attenuated aro A strain of *Salmonella typhimurium*, their application as potential immunogens," Journal of General Microbiology (1991) 137:1557-1564.
Holmgren, J. et al., "Mucosal immunity: implications for vaccine development," Immunobiol. (1992) 184:157-179.
Husseiny, M.L. et al., "Rapid method for the construction *Salmonella enterica* serovar typhimurium vaccine carrier strains," Infec. Immun. (2005) 73(3):1598-1605.
Koch, F. et al., "High level IL-12 production by murine dendritic cells: upregulation via MHC class II and CD40 molecules and downregulation by IL-4 and IL-10," J. Exp. Med. (1996) 184:741-746.

(56) References Cited

OTHER PUBLICATIONS

Kotton, C.N. et al., "Enteric pathogens as vaccine vectors for foreign antigen delivery," Infect. Immun. (2004) 72:5535-5547.
Kwon, Y.M. et al., "*Salmonella* -based vaccines for infectious diseases," Expert Review of Vaccines (2007) 6(2):147-152.
Lavelle, E.C. et al., "Delivery systems and adjuvants for oral vaccines," Expert Opin. Drug Deliv. (2006) 3(6):747-762.
Layton, S.L, et al., "Vaccination of chickens with recombinant *Salmonella* expressing M2e and CD154 epitopes increases protection and decreases viral shedding after low pathogenic avian influenza challenge," Poultry Science (2009) 88(11):2244-2252.
Layton et al., Evaluation of *Salmonella*-vectored Campylobacter peptide epitopes for reduction of Campylobacter jejuni in broiler chickens, Clin. Vaccine Immunol. (2011) 18(3):449-454.
Lee, J.S. et al., "Surface-displayed viral antigens on *Salmonella* carrier vaccine," Nat. Biotechnol. (2000) 18:645-648.
Li, W., "Synergistic antibody induction b antigen-CD40 ligand fusion protein as improved immunogen," Immunology (2005) 115(2):215-222.
Lowe, D.C. et al., "Characterization of candidate live oral *Salmonella typhi* vaccine strains harboring defined mutations in aroA, aroC, and htrA," Infection and Immunity Feb. 1999:700-707.
Mann, J.F. et al., "Delivery systems: a vaccine strategy for overcoming mucosal tolerance?" Expert Rev. Vaccines (2009) 8(1):103-112.
Manoj, S. et al., "Targeting with Bovine CD154 enhances humoral immune responses induced by a DNA vaccine in sheep," (2003) Journal of Immunology 170:989-996.

\* cited by examiner

VACCINE AND METHODS TO REDUCE CAMPYLOBACTER INFECTION

CROSS-REFERENCE TO RELATED APPLICATIONS

This application is a Continuation of U.S. patent application Ser. No. 13/702,827, filed Dec. 7, 2012 issuing on February 24 as U.S. Pat. No. 8,961,990, which is a national stage filing under 35 U.S.C. 371 of International Application No. PCT/US2011/039832, filed Jun. 9, 2011, which claims the benefit of priority of U.S. Provisional Application No. 61/353,039, filed Jun. 9, 2010, all of which are incorporated herein by reference in their entirety.

STATEMENT REGARDING FEDERALLY SPONSORED RESEARCH

This invention was made with government support under grant number 2008-35201-04683, awarded by the National Institute of Food and Agriculture, USDA. The government has certain rights in the invention.

SEQUENCE LISTING

A Sequence Listing accompanies this application and is incorporated herein by reference in its entirety. The Sequence Listing was filed with the application as a text file on Jun. 9, 2011.

BACKGROUND

The repertoire of safe and cost-effective vaccines for generation of mucosal immunity against a variety of agents is limited. The leading bacterial cause of human gastrointestinal disease worldwide is *Campylobacter*. Bacterial gastroenteritis continues to pose a significant threat to the general public in the United States and abroad for the foreseeable future. Infections with *Campylobacter jejuni* occur more frequently than the more publicized infections from *Salmonella* species or *Escherichia coli* O157:H7. The actual burden of illness of *Campylobacter* gastroenteritis nationwide is 500-850 infections/100,000 persons per year.

Not only is *Campylobacter* the leading cause of bacterial gastroenteritis, but *C. jejuni* has been associated with the neuropathological disease Guillain-Barré Syndrome (GBS). This life-threatening disease may be an immune response to ganglioside-like structures on certain *C. jejuni* strains leading to an autoimmune response against nerve cells. Although GBS is the most important chronic sequelae, *Campylobacter* infection is also associated with a reactive arthritis, which may progress to Reiter's syndrome.

Vaccination against *Campylobacter* has had limited success using killed whole-cell or protein based vaccines. In addition, there are concerns regarding the development of Guillain-Barré syndrome or other sequelae from killed whole-cell vaccination. A successful vaccine would need to be cost-effective, safe, orally effective, and be produced in large quantities in a very short time-period. At the present time there is no such vaccine.

SUMMARY

Vectors and methods for enhancing resistance to *Campylobacter* infection or enhancing the immune response to *Campylobacter* are provided herein.

In one aspect, vectors including a first polynucleotide sequence encoding an antigenic polypeptide not natively associated with the vector are provided. The antigenic polypeptide may be SEQ ID NO: 7 (cjaD; cj0113; GVSITVEGNCDEWGTDEYNQA), SEQ ID NO: 8(cjaA; cj0982; KDIVLDAEIGGVAKGKDGKEK) or SEQ ID NO: 9(ACE 393; cj0420; KVALGVAVPKDSNITSV-EDLKDKTLLLNKGTTADA) or a fragment thereof. The vector may also include an immunostimulatory polypeptide not natively associated with the vector. The vaccine vector is capable of eliciting an immune response from a vaccinated subject that includes an IgA antibody response against *Campylobacter*. The response may be protective against challenge with *Campylobacter*.

In another aspect, vectors including a first polynucleotide sequence encoding an antigenic polypeptide not natively associated with the vector and a second polynucleotide sequence encoding an immunostimulatory polypeptide are provided. The antigenic polypeptides may be a fragment of SEQ ID NO: 1 (cjaD), SEQ ID NO: 2 (cjaA) or SEQ ID NO: 3 (ACE393). The vaccine vector is capable of eliciting an immune response from a vaccinated subject that includes an IgA antibody response against *Campylobacter*. The response may be protective against challenge with *Campylobacter*.

In still another aspect, pharmaceutical compositions comprising the vectors provided herein in a pharmaceutically acceptable carrier are disclosed.

In yet another aspect, methods of enhancing an immune response directed to *Campylobacter* in a subject are provided. The methods include administering an effective amount of the vectors provided herein to a subject. In one embodiment, the enhanced immune response includes an IgA antibody response and the response may be protective.

In still a further aspect, methods of enhancing resistance to *Campylobacter* infection are provided herein. The methods include administering an effective amount of the vectors disclosed herein to the subject such that the subject is resistant to infection after subsequent exposure to *Campylobacter*. In one embodiment the enhanced immune response includes an IgA antibody response and the response may be protective.

DETAILED DESCRIPTION

Figure 1:
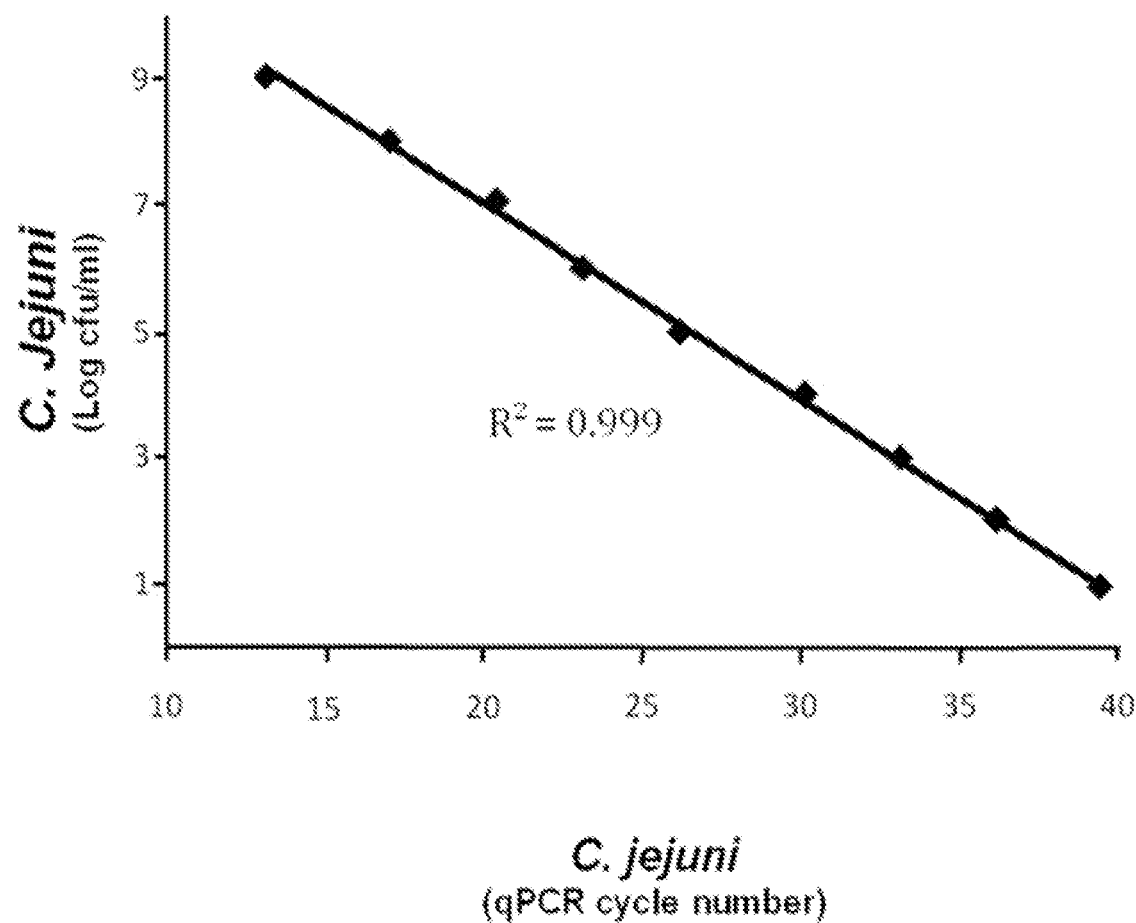
FIG. 1 is a graph showing the standard curve for the quantitative PCR showing the number of cultivable *Campylobacter jejuni* on the x-axis as determined by conventional culturing and determination of colony forming units (CPU). The cycle number at which the fluorescence crossed the threshold in the quantitative PCR is shown on the y axis.

Vaccine vectors that elicit mucosal, humoral, and cell-mediated immune responses against multiple serovars of *Campylobacter* offer a promising approach to limit *Campylobacter* gastroenteritis. This project utilizes a novel approach in the development of vaccines by inserting polynucleotide sequences encoding non-native linear epitopes (antigenic polypeptides). The antigenic polypeptides may be used in combination with an immunostimrnulatory polypeptide such as CD154 (CD40L) or HMGB1 (high mobility group box 1) in the vaccine vector. The antigenic polypeptide and the immunostimulatory polypeptide are suitably not polypeptide found natively associated with the vector. The epitope or antigenic polypeptide and the immunostimulatory polypeptide may be expressed on the surface of recombinant vectors. The vectors may be bacterial, viral or even liposome vectors. The vectors may be live, live and attenuated, or killed prior to administration. Substantial preliminary data, such as that shown in the Examples, demonstrates that *Salmonella* or *Bacillus* constructs expressing a foreign epitope are able to rapidly induce high titer epitope-specific antibodies in vivo. Furthermore, co-expression of surface CD154 or HMGB1 effectively enhanced the antibody response against the foreign epitope.

Recombinant DNA technologies enable relatively easy manipulation of many bacterial and viral species. Some bacteria and viruses are mildly or non-pathogenic, but are capable of generating a robust immune response. These bacteria and viruses make attractive vaccine vectors for eliciting an immune response to a heterologous, non-native, or foreign antigen. Bacterial or viral vaccine vectors may mimic the natural infection and produce robust and long lasting immunity. Vaccine vectors are often relatively inexpensive to produce and administer. In addition, such vectors can often carry more than one antigen and may provide protection against multiple infectious agents.

Polynucleotides encoding polypeptide antigens from any number of pathogenic organisms may be inserted into the vaccine vector and expressed to generate antigenic polypeptides. An antigenic polypeptide is a polypeptide that is capable of being specifically recognized by the adaptive immune system. An antigenic polypeptide includes any polypeptide that is immunogenic. The antigenic polypeptides include, but are not limited to, antigens that are pathogen-related, allergen-related, tumor-related or disease-related. Pathogens include viral, parasitic, fungal and bacterial pathogens as well as protein pathogens such as the prions.

The antigenic polypeptides may be full-length proteins or portions thereof. It is well established that immune system recognition of many proteins is based on a relatively small number of amino acids, often referred to as the epitope. Epitopes may be only 8-10 amino acids. Thus, the antigenic polypeptides described herein may be full-length proteins, 8 amino acid long epitopes or any portion between these extremes. In fact the antigenic polypeptide may include more than one epitope from a single pathogen or protein. Suitably the antigenic polypeptide is a polypeptide that is not natively associated with the vector. Not natively associated includes antigenic polypeptides that may also occur natively in the vector, but that are being expressed recombinantly as an epitope, are being expressed in combination with a different polypeptide as a fusion protein to allow for differential display and differential enhancement of the immune response as compared to the natively expressed polypeptide.

Multiple copies of the same epitope or multiple epitopes from different proteins may be included in the vaccine vector. It is envisioned that several epitopes or antigens from the same or different pathogens or diseases may be administered in combination in a single vaccine vector to generate an enhanced immune response against multiple antigens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time.

The polynucleotides may be inserted into the chromosome of the vaccine vector or encoded on plasmids or other extrachromosomal DNA. Polynucleotides encoding epitopes may be expressed independently (i.e., operably linked to a promoter functional in the vector) or may be inserted into a vaccine vector polynucleotide (i.e., a native polynucleotide or a non-native polynucleotide) that is expressed in the vector. Suitably, the vaccine vector polynucleotide encodes a polypeptide expressed on the surface of the vaccine vector such as a transmembrane protein. The polynucleotide encoding the antigenic polypeptide may be inserted into the vaccine vector polynucleotide sequence in frame to allow expression of the antigenic polypeptide on the surface of the vector. For example, the polynucleotide encoding the antigenic polypeptide may be inserted in frame into a bacterial polynucleotide in a region encoding an external loop region of a transmembrane protein such that the vector polynucleotide sequence remains in frame. See the Examples below in which the antigenic polypeptides are inserted into an external loop of the lamB gene of the *Salmonella enteritidis* vector.

Alternatively, the polynucleotide encoding the antigenic polypeptide may be inserted into a secreted polypeptide. Those of skill in the art will appreciate that the polynucleotide encoding the antigenic polypeptide could be inserted in a wide variety of vaccine vector polynucleotides to provide expression and presentation of the antigenic polypeptide to the immune cells of a subject treated with the vaccine vector. In the Examples, several *Campylobacter* polynucleotides were inserted into the lamB coding sequence of *Salmonella enteritidis*. The resulting recombinant bacteria express the inserted antigenic polypeptides on the surface of the bacteria. The polynucleotides may be inserted in CotB of *Bacillus subtilis* such that the recombinant bacteria expressed the inserted antigenic polypeptides in spores or into sip for surface expression in vegetative bacteria.

The vectors may include a polynucleotide encoding full length *Campylobacter* proteins including cjaD (SEQ ID NO: 1), cjaA (SEQ ID NO: 2) and ACE393 (SEQ ID NO: 3) or an antigenic polypeptide of these proteins. In the Examples, antigenic polypeptides derived from the full-length proteins were used as follows: SEQ ID NO. 7 (a cjaD polypeptide called cj0113); SEQ ID NO: 8 (a cjaA polypeptide called cj0982); and SEQ ID NO: 9 (an ACE 393 polypeptide called cj0420). The polynucleotides used in the Examples are provided as SEQ ID NOs: 4-6, respectively. The polynucleotides used in the Examples had the antigenic polypeptides of SEQ ID NOs 7-9 separated by serine linkers and linked to CD154 amino acids 140-149 (three amino acids before, after and in between the antigenic polypeptide and the immunostimulatory polypeptide).

Suitably, the portion of the antigenic polypeptide inserted into the vaccine vector is immunogenic or antigenic. An immunogenic fragment is a peptide or polypeptide capable of eliciting a cellular or humoral immune response. Suitably, an antigenic polypeptide may be the full-length protein, or suitably may be 20 or more amino acids. 15 or more amino acids, 10 or more amino acids or 8 or more amino acids of the full-length sequence. Suitably the immune response generated against the target pathogen is a protective immune response. A protective immune response is a response capable of blocking or reducing morbidity or mortality caused by subsequent infection with the target pathogen, namely *Campylobacter*.

One of skill in the art will appreciate that any of these polynucleotide sequences may be used in combination with any other antigenic polypeptide including polypeptides from other heterologous pathogens or organisms and may also be used in conjunction with polynucleotides encoding immunostimulatory polypeptides such as a polypeptide of CD154 or HMGB1 such as is described in International Application Nos. PCT/US07/078785 and PCT/US2011/022062 both of which are incorporated herein by reference in their entireties.

Polynucleotides encoding immunostimulatory polypeptides that are homologous to proteins of the subject and capable of stimulating the immune system to respond to the foreign epitope may also be inserted into a vector. As described in more detail below, the vector may include a CD154 polypeptide that is capable of binding CD40 in the subject and stimulating the subject to respond to the vector and its associated foreign antigenic polypeptide. In addition, a vector may include a HMGB1 polypeptide or a functional fragment thereof. As described above with regard to antigenic polypeptides, polynucleotides encoding these polypeptides may be inserted into the chromosome of the vector or maintained extrachromosomally. One of skill in the art will appreciate that these polynucleotides can be inserted in a variety of vector polynucleotides for expression in different parts of the vector or for secretion of the polypeptides.

The polynucleotide encoding an immunostimulatory polypeptide capable of enhancing the immune response to a non-native antigenic polypeptide may also encode the antigenic polypeptide. The polynucleotide encoding an immunostimulatory polypeptide may be linked to the polynucleotide encoding the antigenic polypeptide, such that in the vaccine vector the immunostimulatory polypeptide and the foreign antigenic polypeptide are present on the same polynucleotide. For example, the antigenic polypeptide and the immunostimulatory polypeptide may be portions of a fusion protein. In the Examples, a polynucleotide encoding a polypeptide of CD154 that is capable of binding to CD40 also encodes an antigenic polypeptide from cjaD, cjaA or ACE 393 of *Campylobacter*. See SEQ ID NOS: 10-12 in the attached sequence listing for some examples of potential polypeptide sequences and SEQ ID NOs: 4-6 for polynucleotide sequences which encode for optional serine linkers between the antigenic polypeptide, the immunostimulatory polypeptide and the host polypeptide.

In the Examples, the polynucleotide encoding the *Campylobacter* antigenic polypeptides and the polynucleotide encoding the immunostimulatory polypeptide are both inserted in the outer loop of the transmembrane lamB gene. Those of skill in the art will appreciate that vector polynucleotides encoding other transmembrane proteins may also be used. In addition, the antigenic polynucleotides may be extrachromosomal or secreted by the vector. In the Examples, the polynucleotide encoding the *Campylobacter* cj0113 antigen (SEQ ID NO: 7) and the immunostimulatory peptide HMGB1 (SEQ ID NO:20) were expressed from a plasmid carried by a *Bacillus* vector and expressed on the cell surface.

Suitably, the CD154 polypeptide is fewer than 50 amino acids long, more suitably fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among various species. The CD154 sequences of chicken and human are provided in SEQ ID NO: 13 and SEQ ID NO: 14, respectively.

The CD40 binding regions of CD154 have been determined for a number of species, including human, chicken, duck, mouse and cattle and are shown in SEQ ID NO: 15, SEQ ID NO: 16, SEQ ID NO: 17, SEQ ID NO: 18, and SEQ ID NO:19, respectively. Although there is variability in the sequences in the CD40 binding region between species, cross-species binding of CD154 to CD40 has been reported. For example, the human CD154 polypeptide was able to enhance the immune response in chickens. Therefore, one may practice the invention using species specific CD154 polypeptides or a heterologous CD154 polypeptide.

The HMGB1 (High Mobility Group Box-1) protein was first identified as a DNA-binding protein critical for DNA structure and stability. It is a ubiquitously expressed nuclear protein that binds DNA with no sequence specificity. The protein is highly conserved and found in plants to mammals. The zebrafish, chicken and human HMGB1 amino acid sequences are provided in SEQ ID NO: 28, SEQ ID NO: 20 and SEQ ID NO: 27, respectively. The sequence throughout mammals is highly conserved with 98% amino acid identity and the amino acid changes are conservative. Thus an HMGB1 protein from one species can likely substitute for that from another species functionally. The full-length HMGB1 protein or a portion thereof may be used as the HMGB1 polypeptide in the vaccine vectors described herein. HMGB1 has two DNA binding regions termed A box as shown in SEQ ID NO: 21 and 22 and B box as shown in SEQ ID NO: 23 and 24. See Andersson and Tracey, Annu. Rev. Immunol. 2011, 29:139-162, which is incorporated herein by reference in its entirety.

HMGB1 is a mediator of inflammation and serves as a signal of nuclear damage, such as from necrotic cells. HMGB1 can also be actively secreted by cells of the monocyte/macrophage lineage in a process requiring acetylation of the protein, translocation across the nucleus and secretion. Extracellular HMGB1 acts as a potent mediator of inflammation by signaling via the Receptor for Advanced Glycated End-products (RAGE) and via members of the Toll-like Receptor family (TLR), in particular TLR4. The RAGE binding activity has been identified and requires the polypeptide of SEQ ID NO: 25. TLR4 binding requires the cysteine at position 106 of SEQ ID NO: 20, which is found in the B box region of HMGB1.

The inflammatory activities of HMGB1 do not require the full-length protein and functional fragments have been identified. The B box has been shown to be sufficient to mediate the pro-inflammatory effects of HMGB1 and thus SEQ ID NO: 23 and 24 are HMGB1 polypeptides or functional fragments thereof within the context of the present invention. In addition, the RAGE binding site and the pro-inflammatory cytokine activity have been mapped to SEQ ID NO: 25 and SEQ ID NO: 26, respectively. Thus, these polypeptides are functional fragments of HMGB1 polypeptides in the context of the present invention.

Those of skill in the art are capable of identifying HMGB1 polypeptides and fragments thereof capable of stimulating pro-inflammatory cytokine activity, using methods such as those in International Publication No. WO02 092004, which is incorporated herein by reference in its entirety. Suitably, the HMGB1 polypeptide includes the RAGE binding domain at amino acids 150-183 of SEQ ID NO:20 (SEQ ID NO: 25 or a homolog thereof) and the pro-inflammatory cytokine activity domain between amino acids 89-109 of SEQ ID NO: 20 (SEQ ID NO: 26 or a homolog thereof). In particular, HMGB1 polypeptides and functional fragments or homologs thereof include polypeptides identical to, or at least 99% identical, at least 98% identical, at least 95% identical, at least 90% identical, at least 85% identical, or at least 80% identical to the HMGB1 polypeptides of SEQ ID NOs: 20-28.

One of skill in the art will appreciate that the HMGB1 polypeptide could be used to enhance the immune response to more than one antigenic polypeptide present in a vector. The polypeptide from HMGB1 stimulates an immune response at least in part by activating dendritic cells and macrophages and thus stimulating production of IL-1, IL-6, IFN-γ and TNF-α. Suitably, HMGB1 may be expressed on the surface of the vector.

At least a portion of the antigenic polypeptide and at least a portion of the HMGB1 polypeptide or another immunostimulatory polypeptide may be present on the surface of the vaccine vector. Present on the surface of the vaccine vector includes polypeptides that are comprised within a transmembrane protein, interacting with, covalently or chemically cross-linked to a transmembrane protein, a membrane lipid or membrane anchored carbohydrate. A polypeptide can be comprised within a transmembrane protein by having the amino acids comprising the polypeptide linked via a peptide bond to the N-terminus, C-terminus or anywhere within the transmembrane protein (i.e. inserted between two amino acids of the transmembrane protein or in place of one or more amino acids of the transmembrane protein (i.e. deletion-insertion). Suitably, the polypeptides may be inserted into an external loop of a transmembrane protein. Suitable transmembrane proteins are cotB and lamB, but those of skill in the art will appreciate many suitable transmembrane proteins are available.

Alternatively, the polypeptides may be covalently or chemically linked to proteins, lipids or carbohydrates in the membrane, or capsid if a viral vector is being used through methods available to persons of skill in the art. For example, di-sulfide bonds or biotin—avidin cross-linking could be used to present the antigenic and HMGB1 polypeptides on the surface of a vaccine vector. Suitably, the antigenic polypeptide and the HMGB1 polypeptide are part of a fusion protein. The two polypeptides may be directly linked via a peptide bond or may be separated by a linker or a section of a third protein into which they are inserted.

In the Examples, some of the vectors have the *Campylobacter* antigenic polypeptides (cj0113, cj0420 and cj0982) and the immunostimulatory polypeptide (CD154 amino acids 140-149 or HMGB1 or a functional fragment thereof) encoded on the same polynucleotide (lamB) such that the sequences are in frame with each other and with the *Salmonella* polynucleotide in which they were inserted. In some embodiments, linkers may be added between the polynucleotide sequences encoding the antigenic polypeptide and the immunostimulatory polypeptide such that in the expressed polypeptide several amino acids separate the two polypeptides. The linker may be 3 nucleotides encoding a single amino acid, or may be much longer, e.g. 30 nucleotides encoding 10 or more amino acids. In the Examples a 9 nucleotide linker was used and encoded for three serine residues. Those of skill in the art will readily envision many other types of linkers that could be used.

In addition, the polynucleotides may be present in a single copy or in multiple copies. For example, three copies of the antigenic polypeptide and three copies of the immunostimulatory polypeptide may be found in the same external loop of a transmembrane protein or expressed within several different vector proteins. In alternative embodiments, the immunostimulatory polypeptide and the antigenic polypeptide may be encoded by distinct polynucleotides.

Potential vaccine vectors for use in the methods include, but are not limited to, *Bacillus*, *Salmonella* (*Salmonella enteritidis*), *Shigella*, *Escherichia* (*E. coli*), *Yersinia*, *Bordetella*, *Lactococcus*, *Lactobacillus*, *Streptococcus*, *Vibrio* (*Vi-* brio cholerae), *Listeria*, adenovirus, poxvirus, herpesvirus, alphavirus, and adeno-associated virus. Suitably, the vaccine vector is a GRAS organism. The vaccine vector may be inactivated or killed such that it is not capable of replicating. Methods of inactivating or killing bacterial or viral vaccine vectors are known to those of skill in the art and include, but are not limited to methods such as formalin inactivation, antibiotic-based inactivation, heat treatment and ethanol treatment. In some embodiments the vaccine vector may be a liposome based vector.

Compositions comprising the vector and a pharmaceutically acceptable carrier are also provided. A pharmaceutically acceptable carrier is any carrier suitable for in vivo administration. The pharmaceutically acceptable carrier may include water, buffered solutions, glucose solutions or bacterial culture fluids. Additional components of the compositions may suitably include excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk, and buffers (e.g., phosphate buffer). Especially when such stabilizers are added to the compositions, the composition is suitable for freeze-drying or spray-drying.

Methods of enhancing immune responses to *Campylobacter* in a subject by administering the vectors described herein are also provided. The vector may contain a HMGB1 polypeptide or a CD154 polypeptide capable of stimulating the immune response to the vector and the antigenic polypeptides described above. The vector is administered to a subject in an amount effective to enhance the immune response of the subject to the non-native antigenic polypeptides. Suitably the immune response to challenge with *Campylobacter* is enhanced.

Enhancing an immune response includes, but is not limited to enhancing antibody responses. Suitably the IgA response is enhanced, more suitably the secretory IgA response is enhanced after administration of the vector as compared to a control. The control may be the same subject prior to administration of the vector, a comparable subject administered a vector alone or a vector expressing an irrelevant or a non-*Campylobacter* antigenic polypeptide. The antibody response, suitably the IgA response, may be increased as much as two fold, three fold, four fold, five fold or more as compared to the response of a control subject. The enhanced immune response may also result in a reduction of the ability of *Campylobacter* to grow or replicate and colonize the subject after administration of the vectors described herein. Such a reduction may be tested by challenging a subject administered the vector with a *Campylobacter* infection and monitoring the ability of the bacteria to colonize and replicate, i.e. infect, the subject as compared to a control subject. The growth of *Campylobacter* in the subject may be reduced by 1 log, 2 logs, 3 logs, 4 logs, 5 logs or even more. The growth of *Campylobacter* in a subject administered the vector may be below the level of detection.

In addition, methods of enhancing resistance to *Campylobacter* infection are disclosed. Briefly, the methods comprise administering to a subject the vectors described above comprising *Campylobacter* antigenic polypeptides in an amount effective to elicit an immune response. Enhancing resistance to *Campylobacter* infection includes but is not limited to reducing the incidence of *Campylobacter* infections, limiting the spread of *Campylobacter* infections from one host to another, reducing *Campylobacter* replication in the subject, invasion or spread within a single host, reduced morbidity associated with *Campylobacter* infections, and reduced duration of a *Campylobacter* infection.

Administration of the vector may prevent the subject from contracting *Campylobacter* or from, exhibiting any outward signs of disease, such as gastroenteritis or GBS. Increased resistance to *Campylobacter* may also include increased antibody production, suitably IgA production. The antibody response, suitably the IgA response, may be increased as much, as two fold, three fold, four fold, five fold or more as compared to the response of a control subject. The enhanced immune response may also result in a reduction of the ability of *Campylobacter* to grow or replicate and colonize the subject after administration of the vectors described herein. Such a reduction may be tested by challenging a subject administered the vector with a *Campylobacter* infection and monitoring the ability of the bacteria to colonize and replicate, i.e. infect, the subject as compared to a control subject. The growth of *Campylobacter* in the subject may be reduced by 1 log, 2 logs, 3 logs, 4 logs, 5 logs or even more. The growth of *Campylobacter* in a subject administered the vector may be below the level of detection.

The antigenic polypeptides for use in all the methods described herein may be from cjaD, cjaA or ACE 393 as discussed above. The insertion of the antigenic polypeptides into the vector may be accomplished in a variety of ways known to those of skill in the art, including but not limited to the scarless site-directed mutation system described in International Patent Publication No. WO2008/036675, which is incorporated herein by reference in its entirety. The vector may be a bacterium engineered to express *Campylobacter* antigenic polypeptides in conjunction with polynucleotides capable of enhancing the immune response as discussed above. In particular, a polypeptide of CD154 or HMGB1 may be expressed by the vector to enhance the immune response of the subject to the antigenic polypeptides. The vectors used in these methods may be attenuated or killed prior to administration or use in the methods.

The useful dosage to be administered will vary depending on the age, weight and species of the subject, the mode and route of administration and the type of pathogen against which an immune response is sought. The composition may be administered in any dose of vector sufficient to evoke an immune response. For bacterial vectors, it is envisioned that doses ranging from $10^3$ to $10^{10}$ bacteria, from $10^4$ to $10^9$ bacteria, or from $10^5$ to $10^7$ bacteria are suitable. The composition may be administered only once or may be administered two or more times to increase the immune response. For example, the composition may be administered two or more times separated by one week, two weeks, or by three or more weeks. The bacteria vectors are suitably viable prior to administration, but in some embodiments the bacteria vectors may be killed prior to administration. In some embodiments, the bacteria vectors may be able to replicate in the subject, while in other embodiments the bacteria vectors may be attenuated and/or may not be capable of replicating in the subject.

For administration to animals or humans, the compositions may be administered by a variety of means including, but not limited to, intranasally, mucosally, by spraying, intradermally, parenterally, subcutaneously, orally, by aerosol or intramuscularly. Eye-drop administration or addition to drinking water or food are additionally suitable means of administration. For chickens, the compositions may be administered in ovo.

With regard to the methods, a subject includes, but is not limited to, a vertebrate, suitably a mammal, suitably a human, or birds, suitably poultry such as chickens or turkeys. Other animal models of infection may also be used. Enhancing an immune response includes, but is not limited to, inducing a therapeutic or prophylactic effect that is mediated by the immune system of the subject. For example, an immune response is enhanced if the subject is protected from subsequent infection with *Campylobacter*. Specifically, enhancing an immune response may include enhanced production of antibodies, such as demonstrated in FIGS. 4-8, enhanced class switching of antibody heavy chains, maturation of antigen presenting cells, stimulation of helper T cells, stimulation of cytolytic T cells or induction of T and B cell memory. In the Examples, an increase in the amount of secretory IgA was seen after administration of the vector and was correlated with protection from subsequent *Campylobacter* infection.

It is envisioned that several epitopes or antigens from the same or different pathogens may be administered in combination in a single vector to generate an enhanced immune response against multiple antigens and their associated pathogens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time.

Heterologous polynucleotides encoding antigens can be inserted in the vaccine vector genome at any non-essential site or alternatively may be carried on a plasmid using methods well known in the art. One suitable site for insertion of polynucleotides is within external portions of transmembrane proteins or coupled to sequences which target the heterologous polynucleotide for secretory pathways. One example of a suitable transmembrane protein for insertion of polynucleotides is the lamB gene of *Salmonella*. Heterologous polynucleotides include, but are not limited to, polynucleotides encoding antigens selected from pathogenic microorganisms or viruses other than the vaccine vector, i.e., non-native polynucleotides encoding non-native polypeptides.

The following examples are meant only to be illustrative and are not meant as limitations on the scope of the invention or of the appended claims. All references cited herein are hereby incorporated by reference in their entirety.

EXAMPLES

Attenuation of *Salmonella* Vaccine Candidate Strains

*Salmonella enteritidis* phage type 13A (*S. enteritidis*) was attenuated by introducing defined, irreversible deletion mutations in the aroA and/or htrA gene of the *S. enteritidis* genome as previously described (available as ATCC Deposit Nos: PTA-7871, PTA-7872 and PTA-7873). Briefly, the target gene sequence in the bacterial genome of *S. enteritidis* was replaced with the kanamycm-reslstant ($Km^R$) gene sequence. This was performed using 3S-PCR and electroporation of the 3S-PCR products into electrocompetent *Salmonella* cells containing the pKD46 plasmid. The resulting cell mixture was plated on LB agar plates supplemented with Km to select for positive clones containing a $Km^R$ gene. The $Km^R$ gene was inserted into the genomic region containing the genes of interest (aroA or htrA) by flanking the $Km^R$ gene with sequences homologous to the genes of interest. Once $Km^S$ mutants were obtained, the deletion mutations were confirmed by PCR and DNA sequencing. All $Km^R$ genes were removed before epitope insertion was started.

Construction of Recombinant Vaccine Candidates

Three potential candidate antigenic polypeptides were selected: Omp18/cjaD (cj0113), cjaA (cj0982) and ACE393 (cj0420). The polypeptides selected were as follows: cj0113 (GVSITVEGNCDEWGTDEYNQAWMTTSYAPTS; SEQ ID NO: 10), cj0982c (KDIVLDAEIGGVAKGKDGKE-KWMTTSYAPTS; SEQ ID NO: 11), and cj0420 (KVAL-GVAVPKDSNITSVEDLKDKTLLLNKGTTADAWMTT-SYAPTS; SEQ ID NO: 12), all inserts additionally contain a sequence for amino acids 140-149 of CD154.

Recombinant *S. enteritidis* strains containing stable integrated copies of cj0113-CD154 (cj0113), cj0420-CD154 (cj0420) or cj0982c-CD154 (cj0982) were constructed using the method of Cox et al. Scarless and site-directed mutagenesis in *Salmonella enteritidis* chromosome. BMC Biotechnol 2007; 7:59. Briefly, an I-SceI enzyme site along with a $Km^R$ gene was introduced into Loop 9 of the lamB gene by design of a PCR product which had the I-SceI enzyme site and $Km^R$ gene flanked by approximately 200-300 base pairs of DNA on each side, homologous to the up and downstream regions of Loop 9. Primers used are shown in Table 1 below. The PCR product was electroporated into electrocompetent attenuated *Salmonella* cells containing the pKD46 plasmid and the resulting cell mixture plated on LB agar plates supplemented with Km to select for positive clones now containing a $Km^R$ gene. After the Sce-I/Km mutation was made in Loop 9, this region was replaced by a codon-optimized foreign epitope DNA sequence (Burns D M, Beacham I R. Rare codons in *E. coli* and *S. typhimurium* signal sequences, FEBS Lett 1985; 189(2):318-24). This second 3S-PCR reaction produced the foreign epitope insert flanked by Loop 9 up and downstream regions, and the resulting PCR product was electroporated into electrocompetent SE13A containing the Sce-I/Km mutation described above. Plasmid pBC-I-SceI was also electroporated into the cells along with the insert as the plasmid produces the I-SceI enzyme which recognizes and cleaves a sequence creating a gap at the I-SceI enzyme site in the Loop 9 region of the LamB gene where the foreign epitope sequences inserted into the SE13A genome. The plasmid also carries with it a chloramphenicol (Cm) resistant gene ($Cm^R$) as the inserts that will replace the $Km^R$ gene the mutations must have a new selection marker to counter-select against the previous I-SceI/Km mutation. After electroporation, cells were plated on LB agar plates containing 25 μg/mL Cm for the selection of positive mutants.

TABLE I

PCR Primers

| Primer | Amplified Region | Primer Sequence (SEQ ID NO) |
|---|---|---|
| lam-up-f | Loop 9 up | 5'TGTACAAGTGGACGCCAATC 3' (SEQ ID NO: 29) |
| lam-up-r | Loop 9 up | 5'GTTATCGCCGTCTTTGATATAGCC3' (SEQ ID NO: 30) |

TABLE I-continued

PCR Primers

| Primer | Amplified Region | Primer Sequence (SEQ ID NO) |
|---|---|---|
| lam-dn-f | Loop 9 dn | 5'ATTTCCCGTTATGCCGCAGC3' (SEQ ID NO: 31) |
| lam-dn-r | Loop 9 dn | 5' GTTAAACAGAGGGCGACGAG 3' (SEQ ID NO: 32) |
| Km-f | I-SceI/Km$^r$ gene | 5'GCTATATCAAAGACGGCGATAAC TAACTATAACGGTCCTAAGGTAGCGA ATTTCCGGGGATCCGTCGA 3' (SEQ ID NO: 33) |
| Km-r | I-SceI/Km$^r$ | 5' GCTGCGGCATAACGGGAAA TGTAGGCTGGAGCTGCTTCG 3' (SEQ ID NO: 34) |
| Kan4f | Inside Km$^r$ gene | 5'CAAAAGCGCTCTGAAGTTCC 3' (SEQ ID NO: 35) |
| Kan4r | Inside Km$^r$ gene | 5'GCGTGAGGGGATCTTGAAGT 3' (SEQ ID NO: 36) |
| lam 3f | Outer regions of loop 9 | 5'GCCATCTCGCTTGGTGATAA 3' (SEQ ID NO: 37) |
| lam 3r | Outer regions of loop 9 | 5'CGCTGGTATTTTGCGGTACA 3' (SEQ ID NO: 38) |
| Cj0113f | Insert with loop 9 up | 5'TTCATCGGTACCCCATTCATCACAGTTACCCTTCAACGGTGATGCTAACACCGGAGGAGGAGT TATCGCCGTCTTTGATATAGCC3' (SEQ ID NO: 39) |
| Cj0113r | Insert with loop 9 down | 5'ATGAATGGGGTACCGATGAATATAACCAGGCGTCCTCCTCCTGGATGACCACCTCCTATGCG CCGACCTCCTCCTCCTCCATTTCCCGTTATGCCGCAGC3' (SEQ ID NO: 40) |
| Cj0420f | Insert with loop 9 up | 5'ATCTTTACCTTTCGCAACACCACCGATTTCCGCATCCAGAACGATATCTTTGGAGGAGGAGT TATCGCCGTCTTTGATATAGCC3' (SEQ ID NO: 41) |
| Cj0420r | Insert with loop 9 down | 5'GTGTTGCGAAAGGTAAAGATGGTAAAGAAAAATCCTCCTCCTGGATGACCACCTCCTATGC GCCGACCTCCTCCTCCTCCATTTCCCGTTATGCCGCAGC3' (SEQ ID NO: 42) |
| Cj0982 c-f | Insert with loop 9 up | 5'GGTTTTATCTTTCAGATCTTCAACGCTGGTGATGTTGCTATCTTTCGGAACCGCAACACCCA GCGCAACTTTGGAGGAGGAGTTATCGCCGTCTTTGATATAGCC3' (SEQ ID NO: 43) |
| Cj0982 c-r | Insert with loop 9 down | 5'AAGATCTGAAAGATAAAACCCTGCTGCTGAACAAAGGTACCACCGCGGATGCGTCCTCCTC CTGGATGACCACCTCCTATGCGCCGACCTCCTCCTCCTCCATTTCCCGTTATGCCGCAGC3' (SEQ ID NO: 44) |

Once positive mutation/inserts were suspected, PCR and DNA sequencing were performed to confirm that the insertion, sequences are present and correct.

Challenge with Campylobacter jejuni

Three wild-type isolates of C. jejuni from broiler chickens were individually grown to log-phase growth, combined, serially diluted and spread plated for conventional culture enumeration as previously described (Cole et al. Effect of aeration and storage temperature on Campylobacter concentrations in poultry semen. Poult Sci 2004; 83:1734-8). These were diluted to approximately $10^7$ to $10^8$ cfu/ml tor challenge by oral gavage using spectrophotometric density and comparison to a previously-generated standard curve. Empirically determined cfu administered are reported for each of experiment involving challenge (see below).

Vaccination Study 1

In the first immunization study, 210 day-of-hatch broiler chicks were obtained from a local commercial hatchery and randomly assigned to one of four treatment groups: saline only (Negative control), or one of three vaccine candidate groups: cj0113, cj0420 or cj0982; n=50/pen. Each treatment group was housed in an individual floor pen on fresh pine Litter and provided water and feed ad libitum. On day-of-hatch, all chicks in each treatment group were inoculated, via oral gavage, with 0.25 mL of a solution containing approximately $10^8$ cfu/mL of the appropriate treatment. On day 21 post-hatch, all birds in each treatment group were challenged with C. jejuni, via oral gavage, with 0.25 mL of a solution containing $1 \times 10^7$ cfu/ml. On days 3, 11, 21 (prior to booster inoculation) and 32 post-hatch, 10-15 birds from each treatment group were humanely killed and their liver, spleen and cecal tonsils aseptically removed for the determination of organ invasion, colonization and clearance of the Salmonella vaccine vector strains. Also, on days 21 and 32 post-hatch, ileum sections were removed and processed for use in qRT-PCR and on day 32 a separate ileum sample was removed and diluted 1:5 in saline and was used to test for secretory immunoglobulin A (sIgA). In addition, blood samples were collected from 10 birds per treatment group and the serum was used for determining antibody response on days 21 and 32 post-vaccination.

Vaccination Study 2

In experiment 2, 110 day-of-hatch broiler chicks were obtained from a local commercial hatchery and randomly assigned to one of two treatment groups: saline only (vehicle control) or Salmonella vaccine candidate, cj0113, (n=55/pen). Each treatment group was housed in an individual floor pen on fresh pine litter and provided water and feed ad libitum. On day-of-hatch, all chicks in each treatment group were inoculated via oral gavage with 0.25 mL of a solution containing approximately $10^8$ cfu/mL of the appropriate treatment. On day 21 post-hatch, all birds in each treatment group were challenged with *C. jejuni*, via oral gavage, with 0.25 mL of a solution containing 1×10$^7$ cfu/ml. On days 3, 11, 21 (prior to booster inoculation) and 32 post-hatch, 10-15 birds from each treatment group were humanely killed and their liver, spleen and cecal tonsils aseptically removed for the determination of organ invasion, colonization and clearance of the *Salmonella* vaccine vector strains. Also, on days 21 and 32 post-hatch ileum sections were removed and processed for use in qRT-PCR. In addition, blood samples were collected from 10 birds per treatment group and the serum was used for determining antibody response on days 21 and 32 post-hatch.

Vaccination Study 3

A third experiment was similar to vaccination experiment 2 (described above) except with the addition of a third group of *S. enteriditis* 13A aroA/htrA without the *Campylobacter* epitope (SE13A) as a control for the oral vaccination of the vector itself. All sample collections were the same as vaccination study 2 except on day 32 post-hatch an additional section of ileum was used to harvest the mucosal layer for sIgA as in experiment 1.

Measurement of *Campylobacter* Antibody Response

Serum collected from birds in both immunization studies was used in an ELISA to determine relative antibody responses. Briefly, individual wells of a 96-well plate were coated with *C. jejuni*. Antigen adhesion was allowed to proceed overnight at 4° C., the plates were then washed and blocked with Superblock™ (Pierce) for 1 hour at room temperature. Plates were then incubated for 2 hours with a 1:50 dilution of the previously collected sera. The plates were rinsed again followed by incubation with a Peroxidase-labeled anti-chicken IgG secondary antibody (Jackson Immunolaboratories) for an additional hour. After subsequent rinsing, the plates were developed using a peroxidase substrate kit (BD OpEIA™, Fisher Scientific) and absorbances were read on a spectrophotometer at 450 nm. Each plate contained a positive control and negative control where a pooled sample from vaccinated chicks and pre-immune chicken serum, respectively, replaced the serum from the treatment groups. The absorbance obtained for the positive control, negative control and experimental samples were used to calculate Sample to Positive control ratios (S/P ratios) using the following calculation: (sample mean−negative control mean)/(positive control mean−negative control mean) (Brown et al. Detection of antibodies to Mycoplasma gallisepticum in egg yolk versus serum samples. J Clin Microbiol 1991; 29(12):2901-3 and Davies et al. Evaluation of the use of pooled serum, pooled muscle tissue fluid (meat juice) and pooled faeces for monitoring pig herds for *Salmonella*. J Appl Microbiol 2003; 95(5):1016-25). The ELISA method used for detection of sIgA was similar to the above described assay for serum immunoglobulin except we used goat anti-chicken IgA conjugated with horseradish peroxidase (GenTex) in place of the anti-chicken IgG antibody conjugate.

DNA Isolation and Quantitative PCR for *C. jejuni*

Total DNA extraction from ileal samples was achieved using the QIAmp® DNA Stool Mini Kit (Qiagen). The manufacturer's included protocol was modified slightly in the following ways: ileal contents were removed to include the mucosal layer and diluted 1:5 (w/v) with ice cold PBS+0.05% Tween 20; one ml of the slurry was added to ml of the included ASL Buffer in a 2.0 ml microcentrifuge tube, vortexed and heated to 70° C. for 5 minutes. Subsequently, the manufactures recommendations were followed to the last step when the DNA was eluted into a final volume of 50 ul.

Quantitative determination of *C. jejuni* was accomplished using a previously published method with slight modifications (Skanseng et al. Comparison of chicken gut colonisation by the pathogens *Campylobacter jejuni* and *Clostridium perfringens* by real-time quantitative PCR. Mol Cell Probes 2006; 20(5):269-7)9. The assay was optimized for use on the MX3005P® (Agilent Technology) and Brilliant® II QPCR master mix (Agilent Technologies) all other mixture components, primers, probe and cycling conditions remained as published.

A standard curve (FIG. 1) was prepared using a pure culture of *C. jejuni* serially diluted 10-fold and added to a constant background of ileal content; total DNA isolation was done as previously described.

Statistical Analysis

Data were analyzed using Student's two-tailed t-test assuming unequal variances to compare the difference between groups and controls using JMP™ statistic software. A value of $P<0.05$ was considered significant.

Results

An excellent correlation of quantification of *C. jejuni* using conventional microbiological enumeration techniques verses the qPCR was found (FIG. 1) with a greater than 99% correlation between the two methods. In experiment 1, we observed significant levels of colonization by the three candidate vectored vaccines within the cecal tonsils by day 3 post-vaccination; as well as significant invasion of the internal organs by the cj0113 expressing vector at the same time point (Table II). However, by day 11 post-vaccination, there was a decline in the amount of colonization of all three vectors and by day 21 post-vaccination, the vectors had been completely cleared from the cecal tonsils as well as the internal organs (Table II). We observed the same trend in our follow up vaccination study (experiment 2), using vector-expressed cj0113 as our vaccine candidate, as shown by the data presented in Table II.

TABLE II

Percentage of colonization, invasion and clearance of liver, spleen or cecal tonsils by *Salmonella* following vaccination with one of three *Salmonella* vectored vaccine candidates or saline gavage.

| | Liver/Spleen | | | | Cecal Tonsils | | | |
|---|---|---|---|---|---|---|---|---|
| | Day 3 | Day 11 | Day 21 | Day 32 | Day 3 | Day 11 | Day 21 | Day 32 |
| Experiment 1 | | | | | | | | |
| Saline | 0 | 0 | 0 | 0 | 0 | 0 | 0 | 0 |
| cj0420 | 0 | 0 | 0 | 0 | 60 | 0 | 0 | 0 |
| cj0113 | 50 | 0 | 0 | 0 | 100 | 40 | 0 | 0 |
| cj0982 | 0 | 0 | 0 | 0 | 70 | 20 | 0 | 0 |
| Experiment 2 | | | | | | | | |
| Saline | 0 | 0 | 0 | 0 | 0 | 0 | 0 | 0 |
| cj0113 | 0 | 20 | 0 | 0 | 50 | 40 | 0 | 0 |

In experiments 1 and 2 incidence of the attenuated recombinant *Salmonella* vaccine vector is represented as the percentage of positive liver, spleen, or cecal tonsils out of 10 birds. Chicks were orally gavaged with approximately 10$^8$ cfu of the appropriate treatment on day-of-hatch and. On days 3, 11, 21 and 32 post-hatch, 10 birds from each treatment group were euthanatized, and the livers, spleens, and ceca tonsils were collected for the determination (+/−) of the attenuated recombinant *Salmonella* vaccine vectors. The liver and spleen of each bird were pooled and assayed as one sample.

Figure 2:
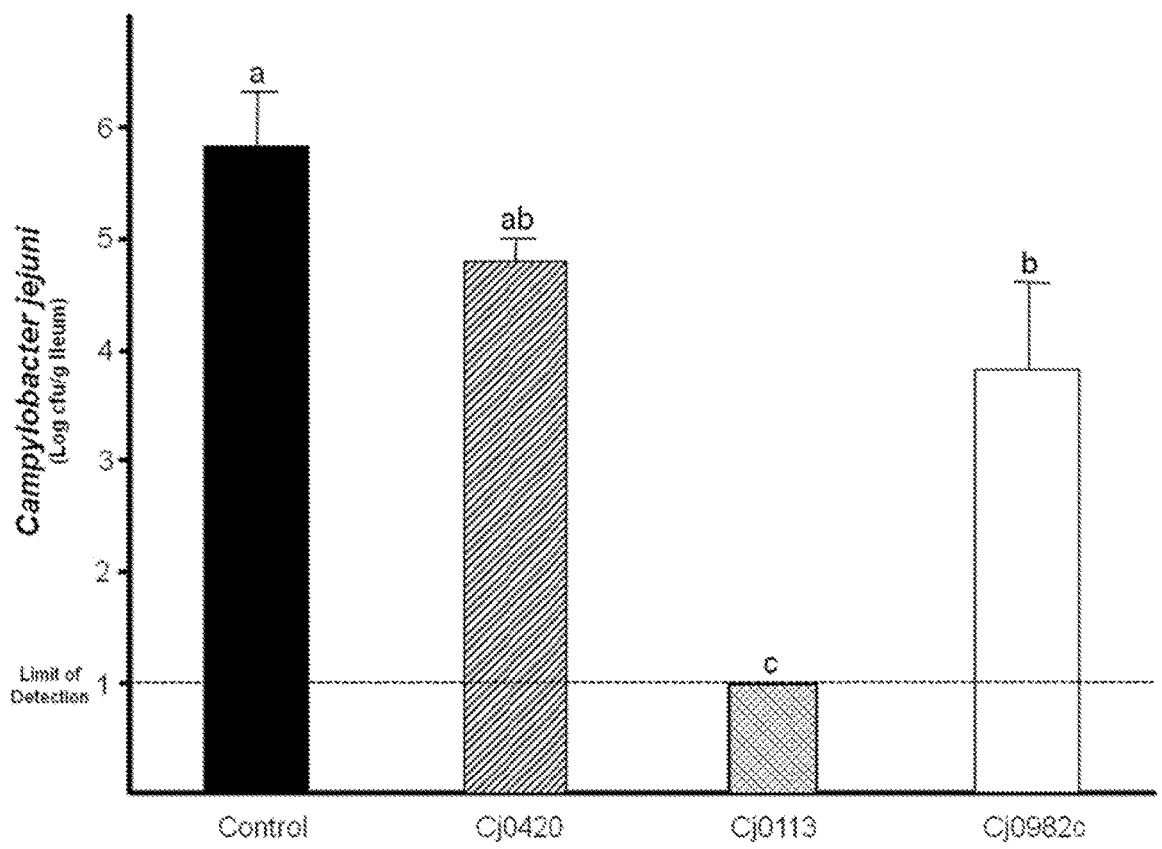
FIG. 2 is a graph showing the log cfu/g ileum content in chicks vaccinated with saline, or *Salmonella* vectors expressing *Campylobacter* peptides cj0420 (SEQ ID NO: 9), cj0113 (SEQ ID NO: 7) or cj0982 (SEQ ID NO: 8) ($10^8$ cfu/chick), 11 days after challenge with *C. jejuni* ($5\times10^7$ cfu/ml). The quantitative PCR was performed on total DNA extracted by conventional methods from mucosal linings of the ileum. The results are presented as mean+/− SEM (n=10). Groups with different lower case letters are significantly different (p0.05).

Chickens were challenged with *C. jejuni* on day 21 post vaccination. Ileal mucosal samples were obtained on days 21 and 32 post vaccination (days 0 and 11 post challenge) and used for DNA sample preparation to enumerate *C. jejuni* within the gut as described above. Vaccination with vector candidates cj0420 and cj0982 caused an approximate 1 log and 2 log reduction ($P<0.05$), respectively, in the level of *C. jejuni* present in the ileal samples. Using the cj0113 vaccine candidate, there was a marked 4.8 log reduction ($P<0.05$) of *C. jejuni* in the ileum compared to the control birds (FIG. 2).

Figure 3:
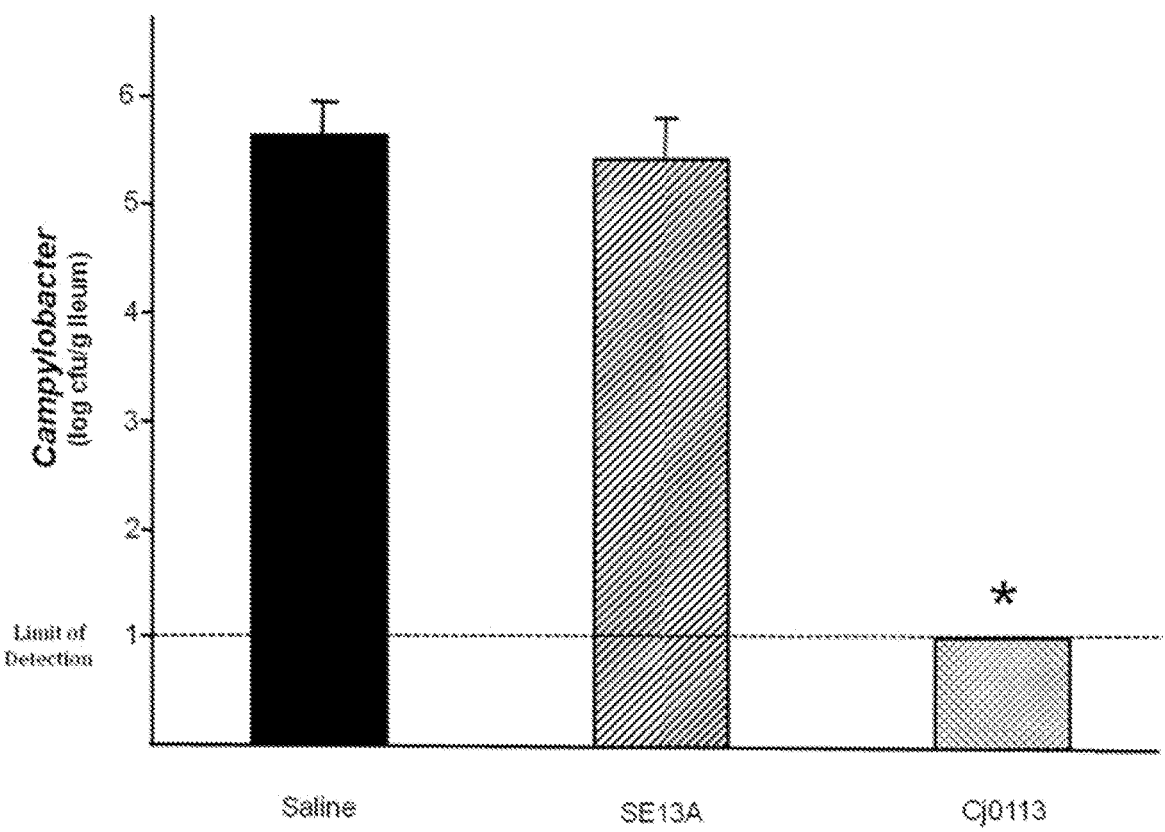
FIG. 3 is a graph showing the log cfu/g ileum content in chicks vaccinated with saline, the *Salmonella* vector without an antigenic polypeptide insert or the *Salmonella* vector with the cj0113 insert (SEQ ID NO: 7) ($10^8$ cfu/chick), 11 days after challenge with *C. jejuni* ($1\times10^7$ cfu/ml). The quantitative PCR was performed on total DNA extracted by conventional methods from mucosal linings of the ileum. The results are presented as mean+/− SEM (n=10) and the * indicates a significant difference (P<0.05).

In experiment 2, a repeat of the primary immunization study was done with only the vaccine candidate expressing cj0113. In this study, qPCR data revealed an approximate 5 log reduction of *C. jejuni* in cj0113 SE-vectored vaccine administered to birds when compared to the birds receiving saline only (Table III). Additionally, in experiment 3 vaccination, with the cj0113 vector caused an approximate 4 log reduction, to below detectable levels, of *C. jejuni* as compared with the saline or *Salmonella* parent strain which contained no epitope insert (FIG. 3).

TABLE III

Enumeration of *Campylobacter jejuni* by quantitative PCR in chicks 11 days following *Campylobacter* challenge in Experiment 2 (n = 10).

| | Mean *C. jejuni* Log10 cfu/gm ileum | $SD^a$ | $SE^b$ |
|---|---|---|---|
| Saline | 5.00 | 0.98 | 0.44 |
| cj0113 | 0.00 | 0.00 | 0.00 |

In experiment 2 *Campylobacter jejuni* quantification was determined in chicks receiving saline or the *Salmonella* vectored vaccine candidate, cj0113 at $10^8$ cfu/chick by quantitative PCR 11 days after receiving a *C. jejuni* challenge dose of approximately $10^7$ cfu/ml. qPCR was performed on total DNA extracted by conventional methods from mucosal linings of the ileum. The results are presented as mean log10 cfu/gram of ileum content with standard deviation[a] and standard error[b] (n = 10).

Figure 4:
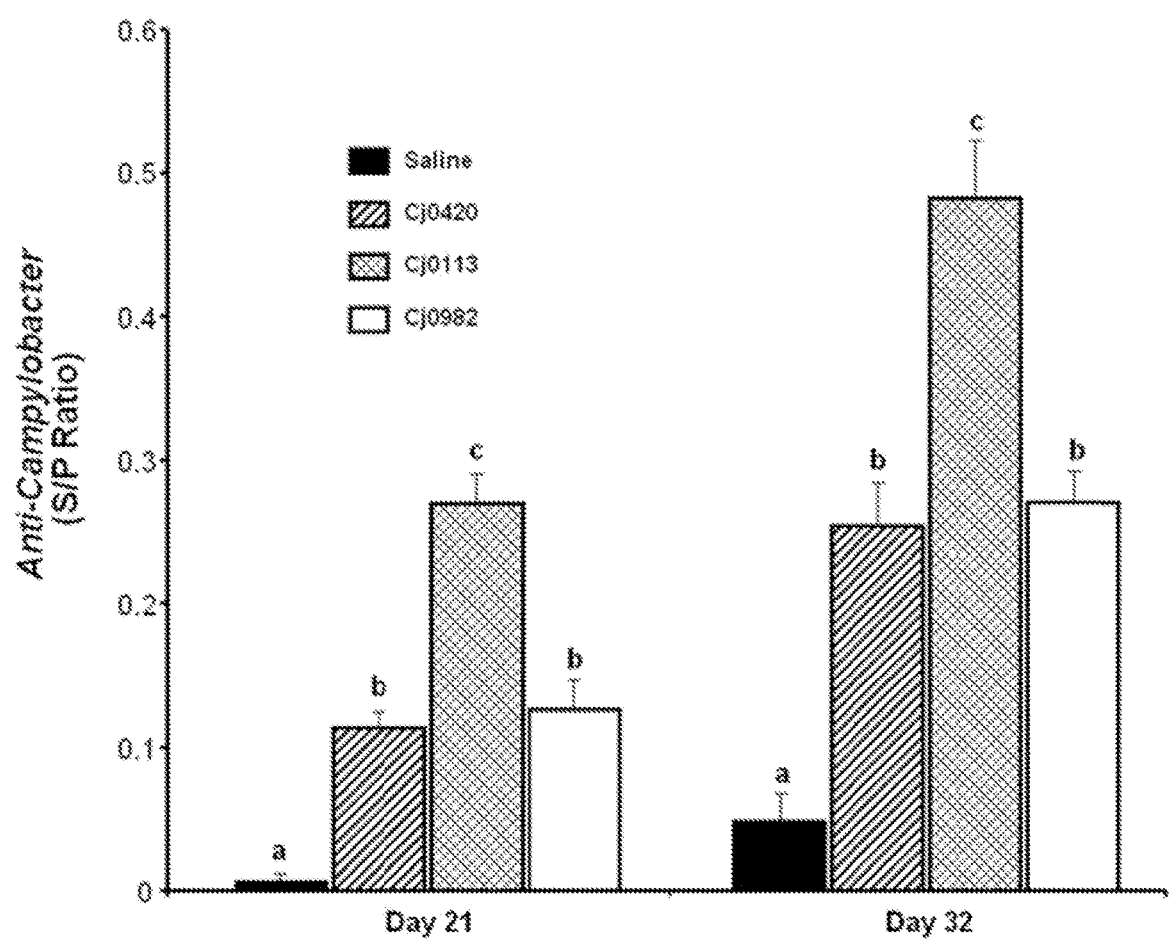
FIG. 4 is a graph showing the relative levels of anti-*Campylobacter* IgG (S/P ratio) as measured by ELISA at days 21 and 32 after administration of the indicated vectors ($10^8$ cfu/chick). Groups with different lower case letters are significantly different (P<0.05).
Figure 5:
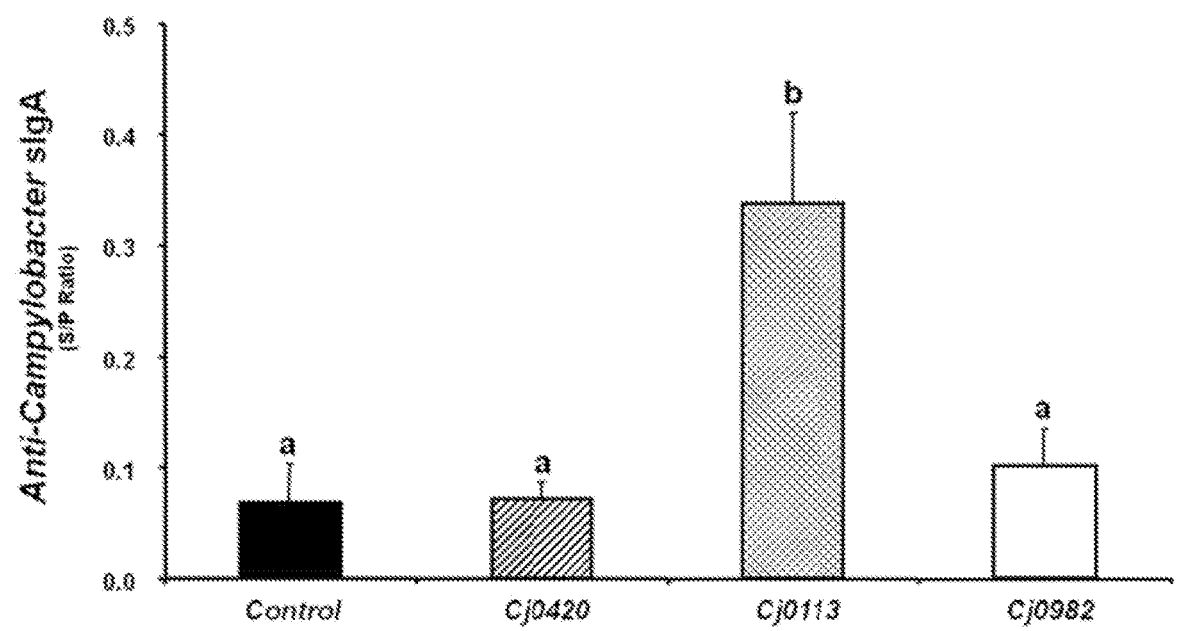
FIG. 5 is a graph showing the relative levels of anti-*Campylobacter* sIgA (S/P ratio) in the mucosa of the ileum on day 32 post-vaccination with the indicated vectors ($10^8$ cfu/chick). Groups with different lower case letters are significantly different (P<0.05).
Figure 6:
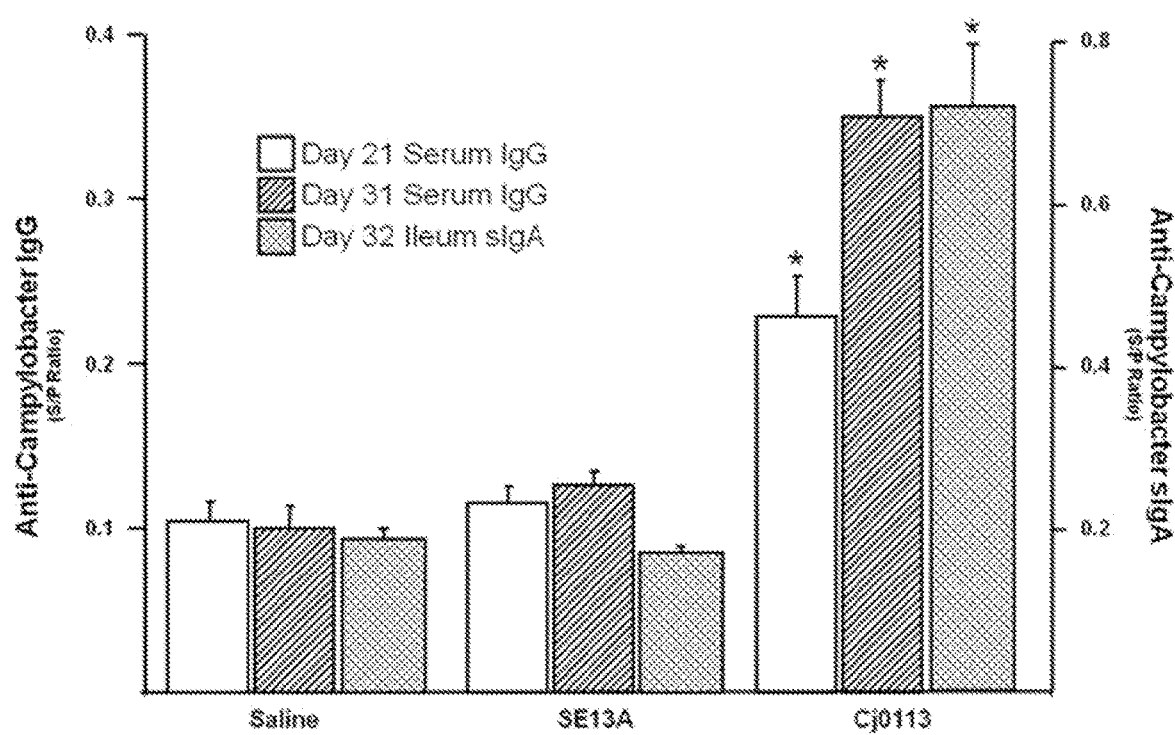
FIG. 6 is a graph showing the serum IgG levels (S/P ratio) at days 21 and 31 post vaccination and sIgA levels (S/P ratio) in the mucosa of the ileum at day 32 post vaccination with saline, the *Salmonella* vector without an insert or the vector with the antigenic polypeptide, cj0113 (SEQ ID NO: 7) ($10^8$ cfu/chick). A * indicates a significant difference from controls (P<0.05).
Figure 7:
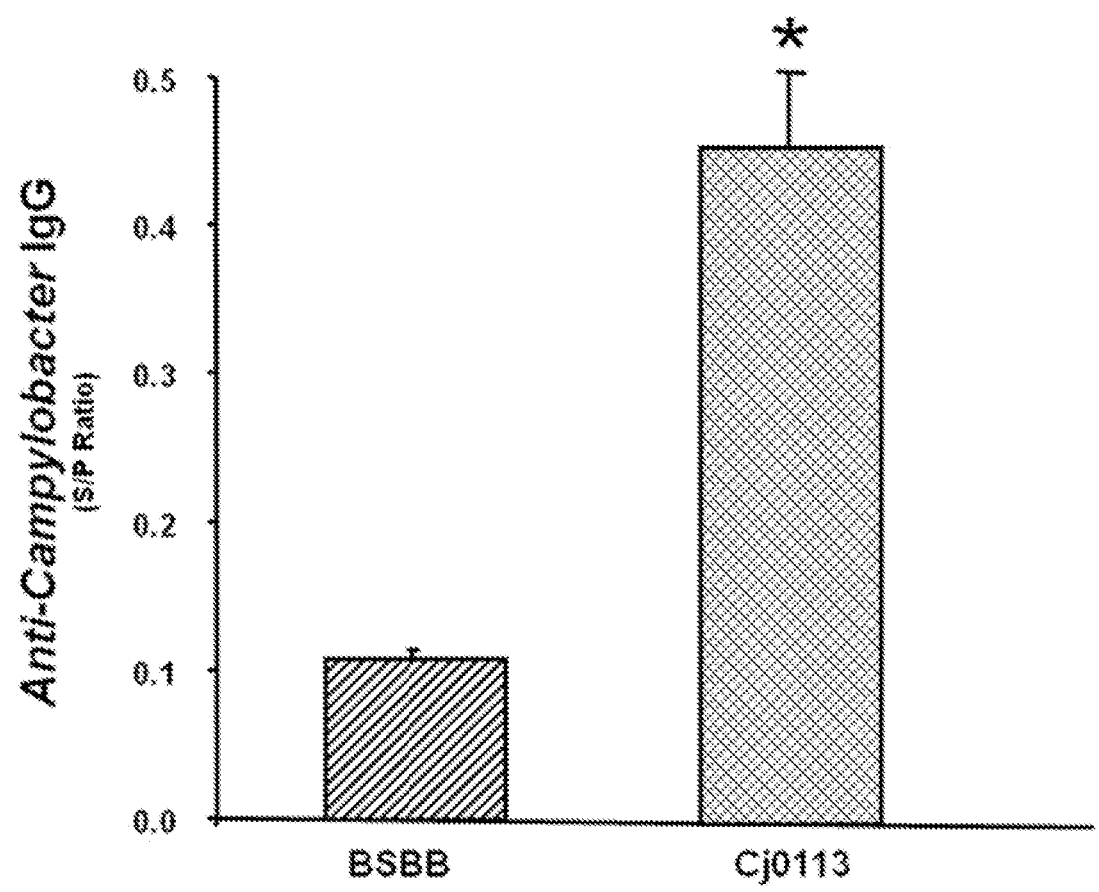
FIG. 7 is a graph showing the *C. jejuni* specific serum IgG antibody levels 10 days post vaccination by oral gavage with either *Bacillus subtitis* backbone strain (BSBB) or cj0113 (SEQ ID NO: 7) *Bacillus subtilis* vectored vaccine candidate at $10^8$ cfu/chick. Data are presented as mean±SEM with the * indicating a significant difference (P<0.05) from both controls.
Figure 8:
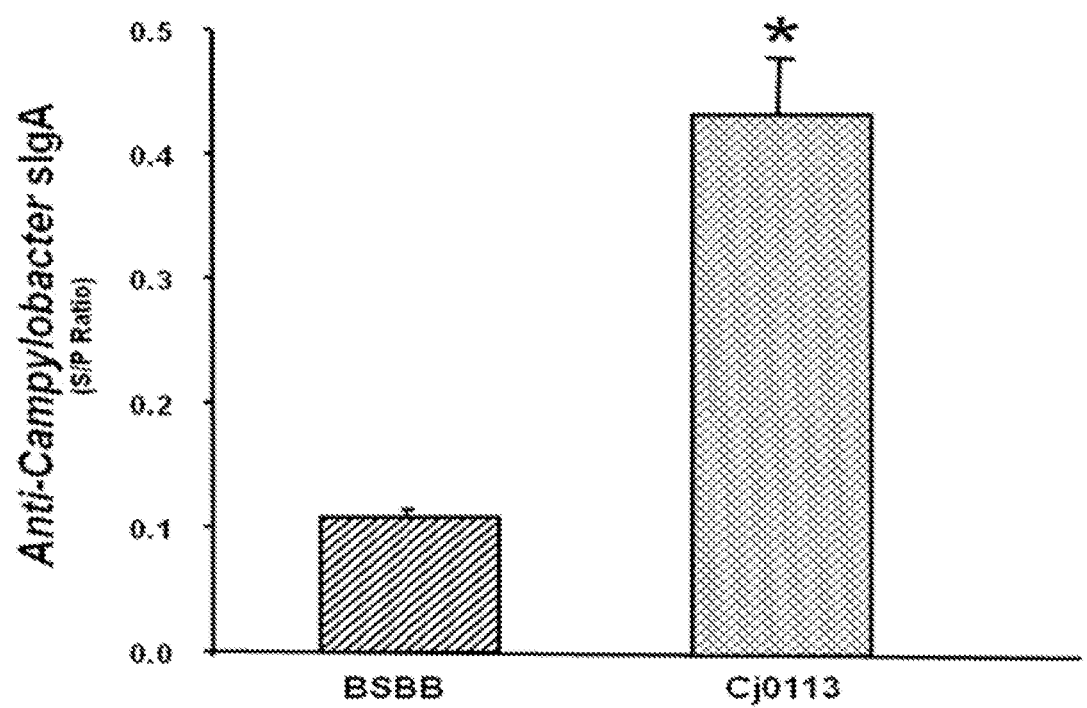
FIG. 8 is a graph showing the *C. jejuni* specific secretory IgA antibody levels 10 days post vaccination by oral gavage with either *Bacillus subtilis* backbone strain (BSBB) or cj0113 (SEQ ID NO: 7) *Bacillus subtilis* vectored vaccine candidate at $10^8$ cfu/chick. The mucosa was collected in the ileum region. Data are presented as mean±SEM with the * indicating a significant difference (P<0.05) from both controls.
Figure 9:
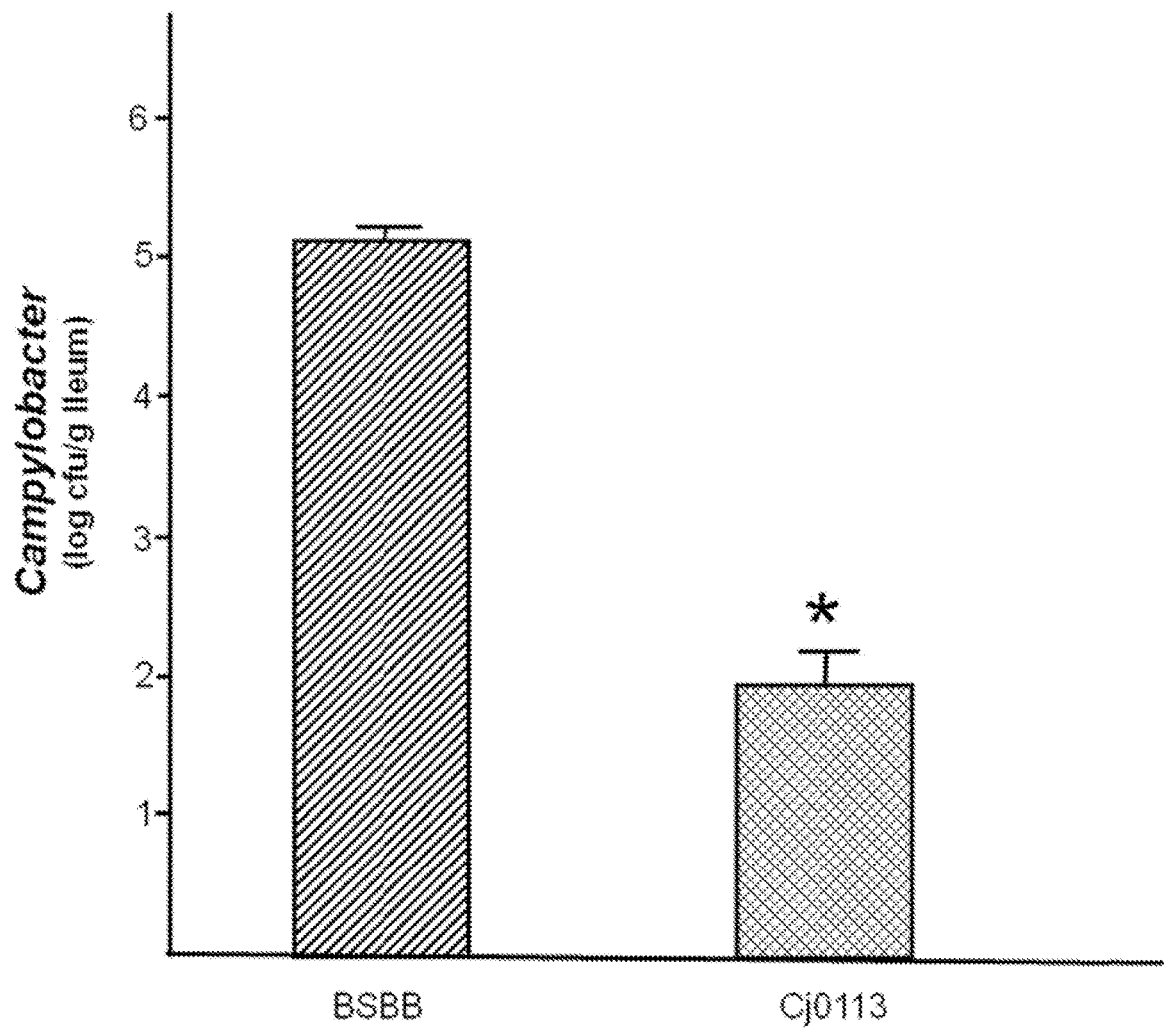
FIG. 9 is a graph showing the $\log_{10}$ CFU of *C. jejuni* per gram of ileum content as enumerated by quantitative PGR. Birds vaccinated with either *Bacillus subtilis* backbone strain (BSBB) or *Bacillus subtilis* vector expressing cj0113 (SEQ ID NO: 7), were challenged with *C. jejuni* at $1 \times 10^8$ cfu/chick then enumerated 10 days after by PCR. qPCR was performed on total DNA extracted by conventional methods from mucosal linings of the ileum. The results are presented as mean $\log_{10}$ cfu/gram of ileum content ±SEM (n=40) and the * indicates a significant difference (P<0.05) from control.
Figure 10:
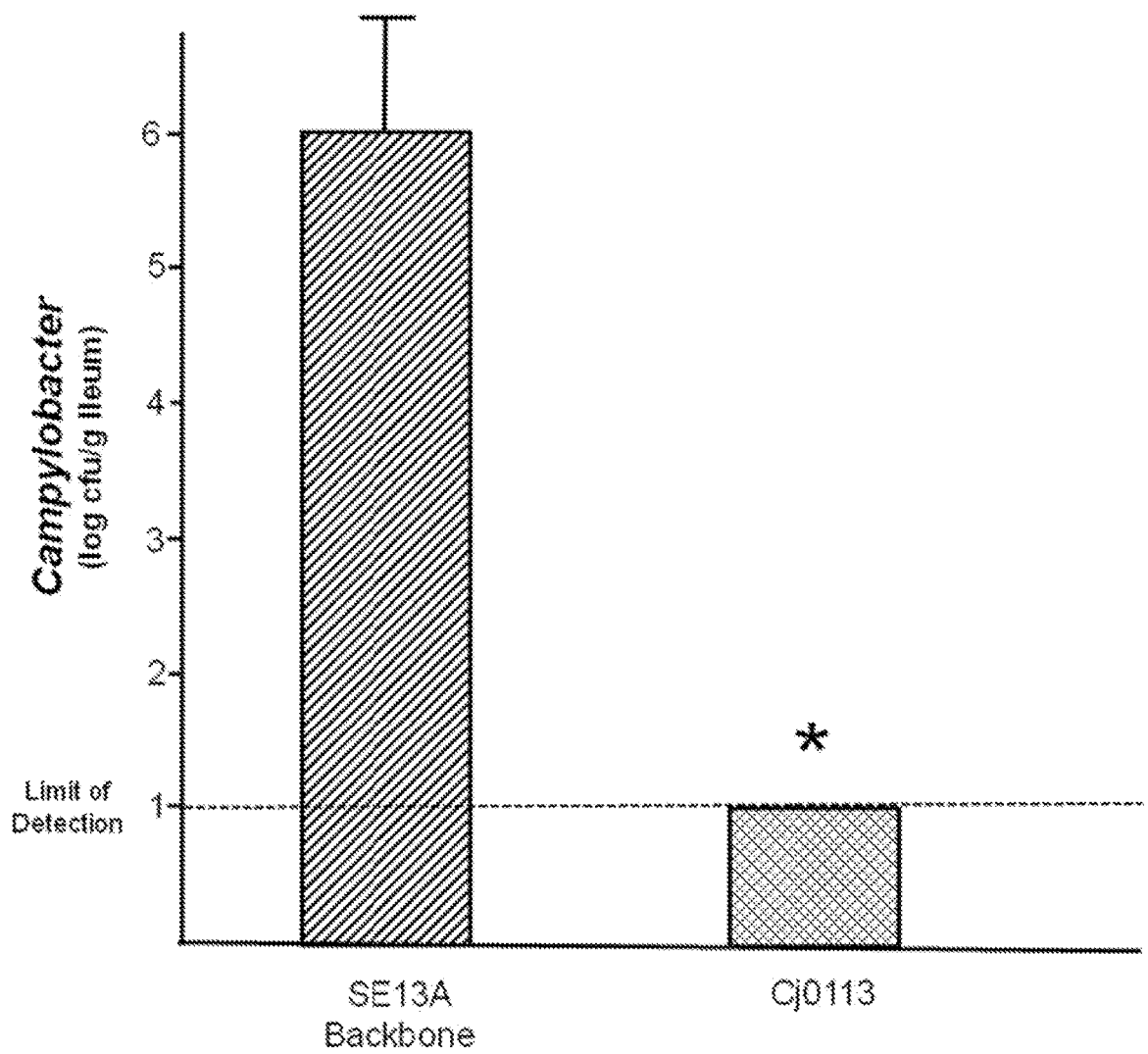
FIG. 10 is a graph showing the $\log_{10}$ CFU of *C. jejuni* per gram of turkey ileum content as enumerated by quantitative PCR. Turkeys vaccinated with either backbone strain or cj0113 (SEQ ID NO: 7) *Salmonella* vectored vaccine, were challenged with *C. coli* at $1 \times 10^8$ cfu/chick then enumerated 12 days after by PGR. qPCR was performed on total DNA extracted fay conventional methods from mucosal linings of the ileum. The results are presented as mean $\log_{10}$ cfu/gram of ileum content ±SEM (n=10) and the * indicates a significant difference (P<0.05) from control.

Serum samples collected in each experiment on Days 21 and 32 post-vaccination were used to determine *C. jejuni*-specific IgG antibodies. In the first experiment all three vaccine candidates (cj0420, cj0113, cj0982) caused significantly higher antibody levels at both time points when compared to the group which received only saline (FIG. 4). Also in the first experiment, the group vaccinated with cj0113 showed significantly higher antibody titers when compared to cj0420 and cj0982 (FIG. 4). An ELISA was also used to determine mucosal sIgA antibody levels specific for *Campylobacter*. These data indicate that the vaccine vector cj0113 caused a significant increase in the levels of sIgA when compared, to the saline group and the two groups receiving either cj0420 or cj0982 (FIG. 5). The results from the second and third study in which only cj0113 was used as a vaccine candidate showed results similar to experiment 1 with vaccinated birds having significantly higher levels of antigen-specific IgG and sIgA antibodies to *C. jejuni* when compared to the birds receiving only saline (Data for Experiment 3 are shown in FIG. 6). Also, in the third experiment the antibody levels for the backbone strain (SE13) were similar to saline controls (FIG. 6).

*Bacillus* Vectored Vaccination Study

Production of Heterologous Proteins for Vegetative Cell Expression

Plasmid pHT10 purchased from MoBioTec/Boca. Scientific, Boca Raton, Fla. (Nguyen et al., 2007) was transformed at the multiple cloning site by addition of a *Bacillus subtilis* codon optimized insertion sequence for cj0113 and HMGB1 (SEQ ID NO: 4 and 20, respectively). DNA sequencing was done to confirm correct sequence insertion. The newly modified plasmid was then transformed into *Bacillus*. Briefly, *Bacillus* cultures were grown overnight at 37° C. in HS media (Spizizen's medium supplemented with 0.5% glucose, 50 μg/ml DL-tryptophan, 50 μg/ml uracil, 0.02% casein hydrolysate, 0.1% yeast extract, 8 μg/ml arginine, 0.4 μg/ml histidine, 1 mM MgSO4). Inoculate 20 ml LS medium (Spizizen's medium supplemented with 0.5% glucose, 5 μg/ml DL-tryptophan, 5 μg/ml uracil, 0.01% casein hydrolysate, 0.1% yeast extract, 1 mM $MgSO_4$ 2.5 mM $MgCl_2$, 0.5 mM $CaCl_2$) with 1 ml overnight culture and incubate with shaking for 3-4 hours at 30° C. Withdraw 1 ml of LS culture and add 10 μl of 0.1M EGTA and incubate at room temperature for 5 minutes. Add 1-2 μg plasmid DNA, shake for 2 hours at 37° C., and plate on LB plates with selective antibiotics. These transformed *Bacillus* spp. now produce heterologous epitope sequences from *Campylobacter* (cj0113) and HMGB1 when induced with 1 mM IPTG.

Vaccination Study

In the vaccination challenge, 100 day-of-hatch broiler chicks were obtained from a local commercial hatchery and randomly assigned to one of four treatment groups: saline only. *Bacillus* vector alone (BSBB) or $10^6$ or $10^8$ *Bacillus* vaccine candidate, cj0113, (n=25/pen). Each treatment group was housed in an individual floor pen on fresh pine litter and provided water and feed ad libitum. On day-of-hatch, all chicks in each treatment group were inoculated via oral gavage with 0.25 mL of a solution containing approximately 1.06 cfu/mL of the backbone vector strain or the Cj0113 *Bacillus* vector. On day 10 birds received a booster vaccination of the same treatment they received on day of hatch. On day 21 post-hatch, all birds in each treatment group were challenged with *C. jejuni*, via oral gavage, with 0.25 mL of a solution containing $1\times10^7$ cfu/ml prepared as described above. On days 3, 11, 21 (prior to booster inoculation) and 32 post-hatch, 10-15 birds from each treatment group were humanely killed and their liver, spleen and cecal tonsils aseptically removed for the determination of organ invasion, colonization and clearance of the vaccine vector strains. Also, on days 21 and 36 post-hatch ileum sections were removed and processed for use in qRT-PCR. In addition, blood samples were collected from 15 birds per treatment group and the serum was used for determining antibody response on days 21 and 36 post-hatch.

Results

Serum samples collected on Day 36 post-vaccination were used to determine *C. jejuni*-specific IgG antibodies. Vaccination with the *bacillus* vector expressing the cj0113 polypeptide caused significantly higher antibody levels when compared to the group which received only saline or empty vector (FIG. 7). An ELISA was also used to determine mucosal sIgA antibody levels specific for *Campylobacter* at day 36 post vaccination. These data indicate that the vaccine vector expressing cj0113 caused a significant increase in the levels of sIgA when compared to the empty vector (FIG. 8).

Chickens were challenged with *C. jejuni* on day 24 post vaccination. Ileal mucosal samples were obtained on days 24 and 36 post vaccination (days 0 and 11 post challenge) and used for DNA sample preparation to enumerate *C. jejuni* within the gut as described above. Vaccination with the *Bacillus* cj0113 vector caused an approximate 3 log reduction ($P<0.05$) in the level of *C. jejuni* present in the ileal samples (FIG. 9).

Vaccination Study in Turkey Poults

Since the *Salmonella*-vectored Cj0113 vaccine has been effective in reducing *Campylobacter* recovery after challenge in chickens we hypothesized that the vaccine may also work in poults. Therefore, to further evaluate the use of this epitope delivery system, an experiment was designed to test the effectiveness of the vaccine against *C. coli* challenge in turkey poults.

The ΔSE-cj0113 vaccine was constructed as described above. *Salmonella enteritidis* phage type 13A (SE13A) was used as the backbone strain for this vaccine candidate. This isolate was double attenuated by irreversible gene deletions in the aroA and htrA genes as previously described. Recombinant strains containing these deletions were then modified further to incorporate the cj0113 insert and an immunostimulatory molecule, CD-154 (ΔSE-cj0113). These sequences were integrated as previously described.

In this experiment, 70 poults were obtained from a local hatchery. They were randomly assigned to one of two treatment groups and tagged. Thirty poults were orally gavaged with $10^8$ cfu/poult ΔSE-cj0113 and the remaining poults were sham treated with saline. On day 21, poults were challenged with $1.5\times10^8$ s cfu/poult of *C. coli* by oral gavage. Liver, spleen and cecal tonsils were aseptically removed on day 3 (N=10), day 21 (N=10) and day 35 (N=10) for detection of vector recovery by enrichment in tetrathionate broth and plating on Brilliant Green agar. On days 21 and 35, ingesta (N=10) and tissue (N=5) samples were collected for further analysis. Ingesta from the Ileum of cultured poults were analyzed using qPCR for enumeration of *C. coli*. Tissue samples from the same region were collected and total RNA was extracted. Interferon-gamma and TNF-alpha like vaccine responses were evaluated.

Results

As previously shown in chickens, the poults developed a significant immune response following vaccination with *Salmonella*-vectored Cj0113 vaccine. After challenge, there was a about a five-log reduction in *Campylobacter coli* in the ileum as compared to vector only controls (FIG. 10). Vaccination with the *Salmonella*-vectored Cj0113 vaccine does appear to work in turkeys similar to the chickens.

We claim:

1. A vaccine vector comprising a first polynucleotide sequence encoding an antigenic polypeptide not natively associated with the vector and a second polynucleotide sequence encoding an HMGB1 polypeptide having at least 98% sequence identity to at least one of SEQ ID NOs: 20, 27 or 28, wherein the antigenic polypeptide consists of SEQ ID NO: 7, or a fragment of SEQ ID NO: 1 comprising SEQ ID NO: 7, wherein the vaccine vector elicits an immune response to *Campylobacter jejuni*.

2. The vaccine vector of claim 1, wherein the vaccine vector is a bacterium.

3. The vaccine vector of claim 2, wherein the bacterium is from a genus selected from *Salmonella, Escherichia, Bacillus* or *Lactobacillus*.

4. The vaccine vector of claim 2, wherein the first polynucleotide sequence and the second polynucleotide sequence are integrated into the genome of the bacterium.

5. The vaccine vector of claim 1, wherein the vaccine vector comprises more than one copy of the first polynucleotide sequence, more than one copy of the second polynucleotide sequence or more than one copy of the first and second polynucleotide sequence.

6. The vaccine vector of claim 1, wherein the first polynucleotide sequence is linked in frame to the second polynucleotide sequence.

7. The vaccine vector of claim 1, wherein the antigenic polypeptide and the HMGB1 polypeptide are expressed on the surface of the vaccine vector.

8. The vaccine vector of claim 7, wherein the first polynucleotide sequence and the second polynucleotide sequence are inserted within a third polynucleotide sequence encoding an external portion of a transmembrane protein.

9. The vector of claim 1, further comprising a second immunostimulatory polypeptide comprising a CD154 polypeptide.

10. The vaccine vector of claim 1, wherein the antigenic polypeptide consists of SEQ ID NO: 7.

11. A method of inducing an immune response in a subject comprising administering the vector of claim 1 to the subject in an amount effective to induce the immune response of the subject to *Campylobacter jejuni*.

12. The method of claim 11, wherein the immune response includes an antibody response to *Campylobacter jejuni*.

13. The method of claim 12, wherein the soluble IgA antibody response to *Campylobacter jejuni* is induced.

14. The method of claim 11, wherein the vector is attenuated or killed prior to administration.

\* \* \* \* \*

SEQUENCE LISTING

```
<160> NUMBER OF SEQ ID NOS: 44

<210> SEQ ID NO 1
<211> LENGTH: 165
<212> TYPE: PRT
<213> ORGANISM: Campylobacter jejuni cjaD

<400> SEQUENCE: 1

Met Lys Lys Ile Leu Phe Thr Ser Ile Ala Ala Leu Ala Val Val Ile
1               5                   10                  15

Ser Gly Cys Ser Thr Lys Ser Thr Ser Val Ser Gly Asp Ser Ser Val
            20                  25                  30

Asp Ser Asn Arg Gly Ser Gly Gly Ser Asp Gly Trp Asp Ile Asp Ser
        35                  40                  45

Lys Ile Ser Gln Leu Asn Asp Thr Leu Asn Lys Val Tyr Phe Asp Phe
    50                  55                  60

Asp Lys Phe Asn Ile Arg Pro Asp Met Gln Asn Val Val Ser Thr Asn
65                  70                  75                  80

Ala Asn Ile Phe Asn Thr Glu Val Ser Gly Val Ser Ile Thr Val Glu
                85                  90                  95

Gly Asn Cys Asp Glu Trp Gly Thr Asp Glu Tyr Asn Gln Ala Leu Gly
            100                 105                 110

Leu Lys Arg Ala Lys Ala Val Lys Glu Ala Leu Ile Ala Lys Gly Val
        115                 120                 125

Asn Ala Asp Arg Ile Ala Val Lys Ser Tyr Gly Glu Thr Asn Pro Val
    130                 135                 140

Cys Thr Glu Lys Thr Lys Ala Cys Asp Ala Gln Asn Arg Arg Ala Glu
145                 150                 155                 160

Phe Lys Leu Ser Arg
                165

<210> SEQ ID NO 2
<211> LENGTH: 279
<212> TYPE: PRT
<213> ORGANISM: Campylobacter jejuni cjaA

<400> SEQUENCE: 2

Met Lys Lys Ile Leu Leu Ser Val Leu Thr Ala Phe Val Ala Val Val
1               5                   10                  15

Leu Ala Ala Cys Gly Gly Asn Ser Asp Ser Lys Thr Leu Asn Ser Leu
            20                  25                  30

Asp Lys Ile Lys Gln Asn Gly Val Val Arg Ile Gly Val Phe Gly Asp
```

```
            35                  40                  45
Lys Pro Pro Phe Gly Tyr Val Asp Glu Lys Gly Asn Asn Gln Gly Tyr
 50                  55                  60

Asp Ile Ala Leu Ala Lys Arg Ile Ala Lys Glu Leu Phe Gly Asp Glu
 65                  70                  75                  80

Asn Lys Val Gln Phe Val Leu Val Glu Ala Asn Arg Val Glu Phe
                 85                  90                  95

Leu Lys Ser Asn Lys Val Asp Ile Ile Leu Ala Asn Phe Thr Gln Thr
                100                 105                 110

Pro Gln Arg Ala Glu Gln Val Asp Phe Cys Ser Pro Tyr Met Lys Val
            115                 120                 125

Ala Leu Gly Val Ala Val Pro Lys Asp Ser Asn Ile Thr Ser Val Glu
        130                 135                 140

Asp Leu Lys Asp Lys Thr Leu Leu Asn Lys Gly Thr Thr Ala Asp
145                 150                 155                 160

Ala Tyr Phe Thr Gln Asn Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Val
            260                 265                 270

Val Ile Glu Gly Gly Lys Ile
        275

<210> SEQ ID NO 3
<211> LENGTH: 190
<212> TYPE: PRT
<213> ORGANISM: Campylobacter jejuni ACE 393

<400> SEQUENCE: 3

Met Lys Lys Val Leu Leu Ser Ser Leu Val Ala Val Ser Leu Leu Ser
 1                   5                  10                  15

Thr Gly Leu Phe Ala Lys Glu Tyr Thr Leu Asp Lys Ala His Thr Asp
                 20                  25                  30

Val Gly Phe Lys Ile Lys His Leu Gln Ile Ser Asn Val Lys Gly Asn
             35                  40                  45

Phe Lys Asp Tyr Ser Ala Val Ile Asp Phe Pro Ala Ser Ala Glu
 50                  55                  60

Phe Lys Lys Leu Asp Val Thr Ile Lys Ile Ala Ser Val Asn Thr Glu
 65                  70                  75                  80

Asn Gln Thr Arg Asp Asn His Leu Gln Gln Asp Asp Phe Phe Lys Ala
                 85                  90                  95

Lys Lys Tyr Pro Asp Met Thr Phe Thr Met Lys Lys Tyr Glu Lys Ile
                100                 105                 110

Asp Asn Glu Lys Gly Lys Met Thr Gly Thr Leu Thr Ile Ala Gly Val
            115                 120                 125
```

```
Ser Lys Asp Ile Val Leu Asp Ala Glu Ile Gly Gly Val Ala Lys Gly
    130                 135                 140

Lys Asp Gly Lys Glu Lys Ile Gly Phe Ser Leu Asn Gly Lys Ile Lys
145                 150                 155                 160

Arg Ser Asp Phe Lys Phe Ala Thr Ser Thr Ser Thr Ile Thr Leu Ser
                165                 170                 175

Asp Asp Ile Asn Leu Asn Ile Glu Val Glu Ala Asn Glu Lys
            180                 185                 190

<210> SEQ ID NO 4
<211> LENGTH: 120
<212> TYPE: DNA
<213> ORGANISM: Campylobacter jejuni cjaD

<400> SEQUENCE: 4
tcctcctccg tgttagcat caccgttgaa ggtaactgtg atgaatgggg taccgatgaa      60
tataaccagg cgtcctcctc ctggatgacc acctcctatg cgccgacctc ctcctcctcc    120

<210> SEQ ID NO 5
<211> LENGTH: 162
<212> TYPE: DNA
<213> ORGANISM: Campylobacter jejuni cjaA

<400> SEQUENCE: 5
tcctcctcca agttgcgct gggtgttgcg gttccgaaag atagcaacat caccagcgtt      60
gaagatctga agataaaac cctgctgctg aacaaaggta ccaccgcgga tgcgtcctcc    120
tcctggatga ccacctccta tgcgccgacc tcctcctcct cc                       162

<210> SEQ ID NO 6
<211> LENGTH: 120
<212> TYPE: DNA
<213> ORGANISM: Campylobacter jejuni ACE 393

<400> SEQUENCE: 6
tcctcctcca agatatcgt tctggatgcg gaaatcggtg gtgttgcgaa aggtaaagat      60
ggtaaagaaa aatcctcctc ctggatgacc acctcctatg cgccgacctc ctcctcctcc    120

<210> SEQ ID NO 7
<211> LENGTH: 21
<212> TYPE: PRT
<213> ORGANISM: Campylobacter jejuni Cj0113

<400> SEQUENCE: 7

Gly Val Ser Ile Thr Val Glu Gly Asn Cys Asp Glu Trp Gly Thr Asp
1               5                   10                  15

Glu Tyr Asn Gln Ala
            20

<210> SEQ ID NO 8
<211> LENGTH: 21
<212> TYPE: PRT
<213> ORGANISM: Campylobacter jejuni Cj0982

<400> SEQUENCE: 8

Lys Asp Ile Val Leu Asp Ala Glu Ile Gly Gly Val Ala Lys Gly Lys
1               5                   10                  15

Asp Gly Lys Glu Lys
            20
```

<210> SEQ ID NO 9
<211> LENGTH: 35
<212> TYPE: PRT
<213> ORGANISM: Campylobacter jejuni Cj0420

<400> SEQUENCE: 9

Lys Val Ala Leu Gly Val Ala Val Pro Lys Asp Ser Asn Ile Thr Ser
1               5                   10                  15

Val Glu Asp Leu Lys Asp Lys Thr Leu Leu Asn Lys Gly Thr Thr
            20                  25                  30

Ala Asp Ala
        35

<210> SEQ ID NO 10
<211> LENGTH: 31
<212> TYPE: PRT
<213> ORGANISM: Artificial Sequence
<220> FEATURE:
<223> OTHER INFORMATION: Synthetic peptide: Cj0113-CD154

<400> SEQUENCE: 10

Gly Val Ser Ile Thr Val Glu Gly Asn Cys Asp Glu Trp Gly Thr Asp
1               5                   10                  15

Glu Tyr Asn Gln Ala Trp Met Thr Thr Ser Tyr Ala Pro Thr Ser
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic peptide: Cj0982-CD154

<400> SEQUENCE: 11

Lys Asp Ile Val Leu Asp Ala Glu Ile Gly Gly Val Ala Lys Gly Lys
1               5                   10                  15

Asp Gly Lys Glu Lys Trp Met Thr Thr Ser Tyr Ala Pro Thr Ser
            20                  25                  30

<210> SEQ ID NO 12
<211> LENGTH: 45
<212> TYPE: PRT
<213> ORGANISM: Artificial Sequence
<220> FEATURE:
<223> OTHER INFORMATION: Synthetic peptide: Cj0420-CD154

<400> SEQUENCE: 12

Lys Val Ala Leu Gly Val Ala Val Pro Lys Asp Ser Asn Ile Thr Ser
1               5                   10                  15

Val Glu Asp Leu Lys Asp Lys Thr Leu Leu Asn Lys Gly Thr Thr
            20                  25                  30

Ala Asp Ala Trp Met Thr Thr Ser Tyr Ala Pro Thr Ser
        35                  40                  45

<210> SEQ ID NO 13
<211> LENGTH: 272
<212> TYPE: PRT
<213> ORGANISM: Gallus gallus
<220> FEATURE:
<221> NAME/KEY: misc_feature
<223> OTHER INFORMATION: CD154 chicken

<400> SEQUENCE: 13

Met Asn Glu Ala Tyr Ser Pro Ala Ala Pro Arg Pro Met Gly Ser Thr

```
             1               5                  10                 15
         Ser Pro Ser Thr Met Lys Met Phe Met Cys Phe Leu Ser Val Phe Met
                         20                 25                 30

Val Val Gln Thr Ile Gly Thr Val Leu Phe Cys Leu Tyr Leu His Met
                         35                 40                 45

Lys Met Asp Lys Met Glu Glu Val Leu Ser Leu Asn Glu Asp Tyr Ile
                     50                 55                 60

Phe Leu Arg Lys Val Gln Lys Cys Gln Thr Gly Glu Asp Gln Lys Ser
         65                  70                 75                 80

Thr Leu Leu Asp Cys Glu Lys Val Leu Lys Gly Phe Gln Asp Leu Gln
                         85                 90                 95

Cys Lys Asp Arg Thr Ala Ser Glu Glu Leu Pro Lys Phe Glu Met His
                        100                105                110

Arg Gly His Glu His Pro His Leu Lys Ser Arg Asn Glu Thr Ser Val
                        115                120                125

Ala Glu Glu Lys Arg Gln Pro Ile Ala Thr His Leu Ala Gly Val Lys
                     130                135                140

Ser Asn Thr Thr Val Arg Val Leu Lys Trp Met Thr Thr Ser Tyr Ala
         145                 150                155                160

Pro Thr Ser Ser Leu Ile Ser Tyr His Glu Gly Lys Leu Lys Val Glu
                        165                170                175

Lys Ala Gly Leu Tyr Tyr Ile Tyr Ser Gln Val Ser Phe Cys Thr Lys
                        180                185                190

Ala Ala Ala Ser Ala Pro Phe Thr Leu Tyr Ile Tyr Leu Tyr Leu Pro
                     195                200                205

Met Glu Glu Asp Arg Leu Leu Met Lys Gly Leu Asp Thr His Ser Thr
                        210                215                220

Ser Thr Ala Leu Cys Glu Leu Gln Ser Ile Arg Glu Gly Gly Val Phe
         225                 230                235                240

Glu Leu Arg Gln Gly Asp Met Val Phe Val Asn Val Thr Asp Ser Thr
                        245                250                255

Ala Val Asn Val Asn Pro Gly Asn Thr Tyr Phe Gly Met Phe Lys Leu
                        260                265                270

<210> SEQ ID NO 14
<211> LENGTH: 261
<212> TYPE: PRT
<213> ORGANISM: Homo sapiens
<220> FEATURE:
<221> NAME/KEY: misc_feature
<223> OTHER INFORMATION: CD154 human

<400> SEQUENCE: 14

Met Ile Glu Thr Tyr Asn Gln Thr Ser Pro Arg Ser Ala Ala Thr Gly
         1                   5                  10                 15

Leu Pro Ile Ser Met Lys Ile Phe Met Tyr Leu Leu Thr Val Phe Leu
                         20                 25                 30

Ile Thr Gln Met Ile Gly Ser Ala Leu Phe Ala Val Tyr Leu His Arg
                         35                 40                 45

Arg Leu Asp Lys Ile Glu Asp Glu Arg Asn Leu His Glu Asp Phe Val
                     50                 55                 60

Phe Met Lys Thr Ile Gln Arg Cys Asn Thr Gly Glu Arg Ser Leu Ser
         65                  70                 75                 80

Leu Leu Asn Cys Glu Glu Ile Lys Ser Gln Phe Glu Gly Phe Val Lys
                         85                 90                 95
```

```
Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 15
<211> LENGTH: 11
<212> TYPE: PRT
<213> ORGANISM: Homo sapiens
<220> FEATURE:
<221> NAME/KEY: misc_feature
<223> OTHER INFORMATION: CD154 partial human

<400> SEQUENCE: 15

Trp Ala Glu Lys Gly Tyr Tyr Thr Met Ser Cys
1               5                   10

<210> SEQ ID NO 16
<211> LENGTH: 11
<212> TYPE: PRT
<213> ORGANISM: Gallus gallus
<220> FEATURE:
<221> NAME/KEY: misc_feature
<223> OTHER INFORMATION: Chicken CD154 peptide

<400> SEQUENCE: 16

Trp Met Thr Thr Ser Tyr Ala Pro Thr Ser Ser
1               5                   10

<210> SEQ ID NO 17
<211> LENGTH: 10
<212> TYPE: PRT
<213> ORGANISM: Anas sp.
<220> FEATURE:
<221> NAME/KEY: misc_feature
<223> OTHER INFORMATION: Duck CD154 peptide

<400> SEQUENCE: 17

Trp Asn Lys Thr Ser Tyr Ala Pro Met Asn
1               5                   10

<210> SEQ ID NO 18
<211> LENGTH: 10
<212> TYPE: PRT
```

<213> ORGANISM: Mus sp.
<220> FEATURE:
<221> NAME/KEY: misc_feature
<223> OTHER INFORMATION: Mouse CD154 peptide

<400> SEQUENCE: 18

Trp Ala Lys Lys Gly Tyr Tyr Thr Met Lys
1               5                   10

<210> SEQ ID NO 19
<211> LENGTH: 10
<212> TYPE: PRT
<213> ORGANISM: Bos taurus
<220> FEATURE:
<221> NAME/KEY: misc_feature
<223> OTHER INFORMATION: Cow CD154 peptide

<400> SEQUENCE: 19

Trp Ala Pro Lys Gly Tyr Tyr Thr Leu Ser
1               5                   10

<210> SEQ ID NO 20
<211> LENGTH: 190
<212> TYPE: PRT
<213> ORGANISM: Gallus gallus
<220> FEATURE:
<221> NAME/KEY: misc_feature
<223> OTHER INFORMATION: Chicken HMGB1 amino acid

<400> SEQUENCE: 20

Met Gly Lys Gly Asp Pro Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Phe Arg Pro Lys
            100                 105                 110

Ile Lys Gly Glu His Pro Gly Leu Ser Ile Gly Asp Val Ala Lys Lys
    115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Glu Glu Glu Asp
            180                 185                 190

<210> SEQ ID NO 21
<211> LENGTH: 85
<212> TYPE: PRT
<213> ORGANISM: Artificial Sequence
<220> FEATURE:
<223> OTHER INFORMATION: Synthetic peptide: HMGB1 box a1

<400> SEQUENCE: 21

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
                35                  40                  45

Trp Lys Thr Met Ser Ser Lys Glu Lys Gly Lys Phe Glu Asp Met Ala
            50                  55                  60

Lys Ala Asp Lys Leu Arg Tyr Glu Lys Glu Met Lys Asn Tyr Val Pro
65                  70                  75                  80

Pro Lys Gly Glu Thr
                85

<210> SEQ ID NO 22
<211> LENGTH: 54
<212> TYPE: PRT
<213> ORGANISM: Artificial Sequence
<220> FEATURE:
<223> OTHER INFORMATION: Synthetic peptide: HMGB1 box a2

<400> SEQUENCE: 22

Pro Asp Ala Ser Val Asn Phe Ser Glu Phe Ser Lys Lys Cys Ser Glu
1               5                   10                  15

Arg Trp Lys Thr Met Ser Ser Lys Glu Lys Gly Lys Phe Glu Asp Met
                20                  25                  30

Ala Lys Ala Asp Lys Leu Arg Tyr Glu Lys Glu Met Lys Asn Tyr Val
                35                  40                  45

Pro Pro Lys Gly Glu Thr
        50

<210> SEQ ID NO 23
<211> LENGTH: 73
<212> TYPE: PRT
<213> ORGANISM: Artificial Sequence
<220> FEATURE:
<223> OTHER INFORMATION: Synthetic peptide: HMGB1 box b1

<400> SEQUENCE: 23

Lys Asp Pro Asn Ala Pro Lys Arg Pro Pro Ser Ala Phe Phe Leu Phe
1               5                   10                  15

Cys Ser Glu Phe Arg Pro Lys Ile Lys Gly Glu His Pro Gly Leu Ser
                20                  25                  30

Ile Gly Asp Val Ala Lys Lys Leu Gly Glu Met Trp Asn Asn Thr Ala
                35                  40                  45

Ala Asp Asp Lys Gln Pro Tyr Glu Lys Lys Ala Ala Lys Leu Lys Glu
            50                  55                  60

Lys Tyr Glu Lys Asp Ile Ala Ala Tyr
65                  70

<210> SEQ ID NO 24
<211> LENGTH: 69
<212> TYPE: PRT
<213> ORGANISM: Artificial Sequence
<220> FEATURE:
<223> OTHER INFORMATION: Synthetic peptide: HMGB1 box b2

<400> SEQUENCE: 24

Asn Ala Pro Lys Arg Pro Pro Ser Ala Phe Phe Leu Phe Cys Ser Glu
1               5                   10                  15

Phe Arg Pro Lys Ile Lys Gly Glu His Pro Gly Leu Ser Ile Gly Asp
            20                  25                  30

Val Ala Lys Leu Gly Glu Met Trp Asn Asn Thr Ala Ala Asp Asp
        35                  40                  45

Lys Gln Pro Tyr Glu Lys Ala Ala Lys Leu Lys Glu Lys Tyr Glu
    50                  55                  60

Lys Asp Ile Ala Ala
65

<210> SEQ ID NO 25
<211> LENGTH: 21
<212> TYPE: PRT
<213> ORGANISM: Artificial Sequence
<220> FEATURE:
<223> OTHER INFORMATION: Synthetic peptide: HMGB1 RAGE Binding domain

<400> SEQUENCE: 25

Lys Asp Pro Asn Ala Pro Lys Arg Pro Pro Ser Ala Phe Phe Leu Phe
1               5                   10                  15

Cys Ser Glu Phe Arg
            20

<210> SEQ ID NO 26
<211> LENGTH: 33
<212> TYPE: PRT
<213> ORGANISM: Artificial Sequence
<220> FEATURE:
<223> OTHER INFORMATION: Synthetic peptide: HMGB1 proinflammatory
      cytokine activity

<400> SEQUENCE: 26

Leu Lys Glu Lys Tyr Glu Lys Asp Ile Ala Ala Tyr Arg Ala Lys Gly
1               5                   10                  15

Lys Val Asp Ala Gly Lys Lys Val Val Ala Lys Ala Glu Lys Ser Lys
            20                  25                  30

Lys

<210> SEQ ID NO 27
<211> LENGTH: 215
<212> TYPE: PRT
<213> ORGANISM: Homo sapiens
<220> FEATURE:
<221> NAME/KEY: misc_feature
<223> OTHER INFORMATION: HMGB1

<400> SEQUENCE: 27

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

```
Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Glu Asp Glu Asp
            195                 200                 205

Glu Glu Asp Asp Asp Asp Glu
        210                 215

<210> SEQ ID NO 28
<211> LENGTH: 205
<212> TYPE: PRT
<213> ORGANISM: Danio rerio
<220> FEATURE:
<221> NAME/KEY: misc_feature
<223> OTHER INFORMATION: Zebra fish HMGB1

<400> SEQUENCE: 28

Met Gly Lys Asp Pro Thr Lys Pro Arg Gly Lys Met Ser Ser Tyr Ala
1               5                   10                  15

Tyr Phe Val Gln Thr Cys Arg Glu Glu His Lys Lys His Pro Glu
            20                  25                  30

Ala Thr Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
50                  55                  60

Leu Asp Lys Ala Arg Tyr Glu Arg Glu Met Lys Asn Tyr Ile Pro Pro
65                  70                  75                  80

Lys Gly Glu Lys Lys Lys Arg Phe Lys Asp Pro Asn Ala Pro Lys Arg
                85                  90                  95

Pro Pro Ser Ala Phe Phe Ile Phe Cys Ser Glu Phe Arg Pro Lys Val
            100                 105                 110

Lys Glu Glu Thr Pro Gly Leu Ser Ile Gly Asp Val Ala Lys Arg Leu
        115                 120                 125

Gly Glu Met Trp Asn Lys Ile Ser Ser Glu Glu Lys Gln Pro Tyr Glu
130                 135                 140

Lys Lys Ala Ala Lys Leu Lys Glu Lys Tyr Glu Lys Asp Ile Ala Ala
145                 150                 155                 160

Tyr Arg Ser Lys Gly Lys Val Gly Gly Gly Ala Ala Lys Ala Pro Ser
                165                 170                 175

Lys Pro Asp Lys Ala Asn Asp Glu Asp Glu Asp Glu Glu Glu
            180                 185                 190

Asp Glu Asp Asp Asp Asp Glu Glu Glu Asp Asp Glu
        195                 200                 205

<210> SEQ ID NO 29
<211> LENGTH: 20
<212> TYPE: DNA
<213> ORGANISM: Artificial Sequence
<220> FEATURE:
<223> OTHER INFORMATION: Synthetic primer: lam-up-f; Loop 9 up
```

<400> SEQUENCE: 29
tgtacaagtg gacgccaatc                                          20

<210> SEQ ID NO 30
<211> LENGTH: 24
<212> TYPE: DNA
<213> ORGANISM: Artificial Sequence
<220> FEATURE:
<223> OTHER INFORMATION: Synthetic primer: lam-up-r; Loop 9 up

<400> SEQUENCE: 30
gttatcgccg tctttgatat agcc                                     24

<210> SEQ ID NO 31
<211> LENGTH: 20
<212> TYPE: DNA
<213> ORGANISM: Artificial Sequence
<220> FEATURE:
<223> OTHER INFORMATION: Synthetic primer: lam-dn-f; Loop 9 dn

<400> SEQUENCE: 31
atttcccgtt atgccgcagc                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer: lam-dn-r; Loop 9 dn

<400> SEQUENCE: 32
gttaaacaga gggcgacgag                                          20

<210> SEQ ID NO 33
<211> LENGTH: 68
<212> TYPE: DNA
<213> ORGANISM: Artificial Sequence
<220> FEATURE:
<223> OTHER INFORMATION: Synthetic primer: Km-f; I-SceI/Kmr gene

<400> SEQUENCE: 33
gctatatcaa agacggcgat aactaactat aacggtccta aggtagcgaa tttccgggga   60
tccgtcga                                                       68

<210> SEQ ID NO 34
<211> LENGTH: 39
<212> TYPE: DNA
<213> ORGANISM: Artificial Sequence
<220> FEATURE:
<223> OTHER INFORMATION: Synthetic primer: Km-r; I-SceI/Kmr gene

<400> SEQUENCE: 34
gctgcggcat aacgggaaat gtaggctgga gctgcttcg                     39

<210> SEQ ID NO 35
<211> LENGTH: 20
<212> TYPE: DNA
<213> ORGANISM: Artificial Sequence
<220> FEATURE:
<223> OTHER INFORMATION: Synthetic primer: Kan4f; Inside Kmr gene

<400> SEQUENCE: 35
caaaagcgct ctgaagttcc                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer: Kan4r; Inside Kmr gene

<400> SEQUENCE: 36
gcgtgagggg atcttgaagt                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer: lam 3f; Outer regions of
      loop 9

<400> SEQUENCE: 37
gccatctcgc ttggtgataa                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic primer: lam 3r; Outer regions of
      loop 9

<400> SEQUENCE: 38
cgctggtatt ttgcggtaca                                          20

<210> SEQ ID NO 39
<211> LENGTH: 84
<212> TYPE: DNA
<213> ORGANISM: Artificial Sequence
<220> FEATURE:
<223> OTHER INFORMATION: Synthetic primer: Cj0113f; Insert with loop 9
      up

<400> SEQUENCE: 39
ttcatcggta ccccattcat cacagttacc ttcaacggtg atgctaacac cggaggagga      60
gttatcgccg tctttgatat agcc                                            84

<210> SEQ ID NO 40
<211> LENGTH: 100
<212> TYPE: DNA
<213> ORGANISM: Artificial Sequence
<220> FEATURE:
<223> OTHER INFORMATION: Synthetic primer: Cj0113r; Insert with loop 9
      down

<400> SEQUENCE: 40
atgaatgggg taccgatgaa tataaccagg cgtcctcctc ctggatgacc acctcctatg      60
cgccgacctc ctcctcctcc atttcccgtt atgccgcagc                          100

<210> SEQ ID NO 41
<211> LENGTH: 84
<212> TYPE: DNA
<213> ORGANISM: Artificial Sequence
<220> FEATURE:
<223> OTHER INFORMATION: Synthetic primer: Cj0420f; Insert with loop 9
      up

<400> SEQUENCE: 41

```
atctttacct ttcgcaacac caccgatttc cgcatccaga acgatatctt tggaggagga      60
gttatcgccg tctttgatat agcc                                            84

<210> SEQ ID NO 42
<211> LENGTH: 100
<212> TYPE: DNA
<213> ORGANISM: Artificial Sequence
<220> FEATURE:
<223> OTHER INFORMATION: Synthetic primer: Cj0420r; Insert with loop 9
      down

<400> SEQUENCE: 42
gtgttgcgaa aggtaaagat ggtaaagaaa aatcctcctc ctggatgacc acctcctatg      60
cgccgacctc ctcctcctcc atttcccgtt atgccgcagc                          100

<210> SEQ ID NO 43
<211> LENGTH: 105
<212> TYPE: DNA
<213> ORGANISM: Artificial Sequence
<220> FEATURE:
<223> OTHER INFORMATION: Synthetic primer: Cj0982c-f; Insert with loop
      9 up

<400> SEQUENCE: 43
ggttttatct ttcagatctt caacgctggt gatgttgcta tctttcggaa ccgcaacacc      60
cagcgcaact ttggaggagg agttatcgcc gtctttgata tagcc                    105

<210> SEQ ID NO 44
<211> LENGTH: 121
<212> TYPE: DNA
<213> ORGANISM: Artificial Sequence
<220> FEATURE:
<223> OTHER INFORMATION: Synthetic primer: Cj0982c-r; Insert with loop
      9 down

<400> SEQUENCE: 44
aagatctgaa agataaaacc ctgctgctga acaaaggtac caccgcggat gcgtcctcct      60
cctggatgac cacctcctat gcgccgacct cctcctcctc catttcccgt tatgccgcag    120
c                                                                    121
```